United States Patent
Walsh et al.

(10) Patent No.: US 10,806,580 B2
(45) Date of Patent: *Oct. 20, 2020

(54) SELF-ADJUSTING ATTACHMENT STRUCTURE FOR A CARDIAC SUPPORT DEVICE

(71) Applicant: Mardil, Inc., Champlin, MN (US)

(72) Inventors: Robert G. Walsh, Lakeville, MN (US); Aaron J. Hjelle, Champlin, MN (US); Paul Andrew Pignato, Stacy, MN (US); Ann Margaret Thomas, Plymouth, MN (US); Hani N. Sabbah, Waterford, MI (US); Noreen Walen Thompson, Arden Hills, MN (US); Holly J. Hermeling, Minnetonka, MN (US)

(73) Assignee: Mardil, Inc., Champlin, MN (US)

( * ) Notice: Subject to any disclaimer, the term of this patent is extended or adjusted under 35 U.S.C. 154(b) by 126 days.

This patent is subject to a terminal disclaimer.

(21) Appl. No.: 15/682,203

(22) Filed: Aug. 21, 2017

(65) Prior Publication Data
US 2018/0028316 A1 Feb. 1, 2018

Related U.S. Application Data

(63) Continuation of application No. 13/048,588, filed on Mar. 15, 2011, now Pat. No. 9,737,403, which is a continuation of application No. 12/701,302, filed on Feb. 5, 2010, now abandoned, which is a continuation of application No. 11/368,257, filed on Mar. 3, 2006, now abandoned.

(51) Int. Cl.
*A61F 2/24* (2006.01)

(52) U.S. Cl.
CPC ................. *A61F 2/2481* (2013.01)

(58) Field of Classification Search
CPC . A61F 2/2478; A61F 2/2481; A61F 2002/249
See application file for complete search history.

(56) References Cited

U.S. PATENT DOCUMENTS

| | | | |
|---|---|---|---|
| 1,682,119 | A | 8/1928 | Field |
| 1,965,542 | A | 11/1933 | Colvin, Jr. |
| 1,982,207 | A | 11/1934 | Furniss |
| 2,138,603 | A | 11/1938 | Johnson |
| 2,278,926 | A | 4/1942 | Hartwell |

(Continued)

FOREIGN PATENT DOCUMENTS

| | | |
|---|---|---|
| DE | 324524 | 8/1920 |
| DE | 3831540 | 4/1989 |

(Continued)

OTHER PUBLICATIONS

U.S. Appl. No. 09/635,345, filed Aug. 2000, Chin.

(Continued)

*Primary Examiner* — Catherine B Kuhlman
(74) *Attorney, Agent, or Firm* — Fish & Richardson P.C.

(57) ABSTRACT

A cardiac support device includes a jacket and elastic attachment structure for self-securing the jacket to a heart. The attachment structures can include undulating metal and polymer elements, a silicone band and elastomeric filaments on a base end of the jacket.

9 Claims, 17 Drawing Sheets

(56) References Cited

U.S. PATENT DOCUMENTS

| | | | |
|---|---|---|---|
| 2,376,442 | A | 5/1945 | Mehler |
| 2,992,550 | A | 7/1961 | Frith |
| 3,384,530 | A | 5/1968 | Mercer et al. |
| 3,452,742 | A | 7/1969 | Muller |
| 3,551,543 | A | 12/1970 | Mercer et al. |
| 3,587,567 | A | 6/1971 | Schiff |
| 3,643,301 | A * | 2/1972 | Weigl .............. D04H 1/4258 28/155 |
| 3,732,662 | A | 5/1973 | Paxton |
| 3,768,643 | A | 10/1973 | Bruno |
| 3,811,411 | A | 5/1974 | Moeller |
| 3,983,863 | A | 10/1976 | Janke et al. |
| 4,035,849 | A | 7/1977 | Angell |
| 4,048,990 | A | 9/1977 | Goetz |
| 4,196,534 | A | 4/1980 | Shibamoto |
| 4,403,604 | A | 9/1983 | Wilkinson et al. |
| 4,428,375 | A | 1/1984 | Ellman |
| D273,514 | S | 4/1984 | Heilman et al. |
| 4,466,331 | A | 8/1984 | Matheson |
| 4,536,893 | A | 8/1985 | Parravicini |
| 4,567,900 | A | 2/1986 | Moore |
| 4,598,039 | A | 7/1986 | Fischer et al. |
| 4,630,597 | A | 12/1986 | Kantrowitz et al. |
| 4,637,377 | A | 1/1987 | Loop |
| 4,690,134 | A | 9/1987 | Snyders |
| 4,790,850 | A | 12/1988 | Dunn et al. |
| 4,821,723 | A | 4/1989 | Baker, Jr. et al. |
| 4,827,932 | A | 5/1989 | Ideker et al. |
| 4,834,707 | A | 5/1989 | Evans |
| 4,840,626 | A | 6/1989 | Linsky et al. |
| 4,878,890 | A | 11/1989 | Bilweis |
| 4,932,972 | A | 6/1990 | Dunn et al. |
| 4,936,857 | A | 6/1990 | Kulik |
| 4,957,477 | A | 9/1990 | Lundback |
| 4,973,300 | A | 11/1990 | Wright |
| 4,976,730 | A | 12/1990 | Kwan-Gett |
| 4,984,584 | A | 1/1991 | Hansen et al. |
| 4,995,857 | A | 2/1991 | Arnold |
| 5,042,463 | A | 8/1991 | Lekholm |
| 5,057,117 | A | 10/1991 | Atweh |
| 5,064,431 | A * | 11/1991 | Gilbertson .......... A61F 2/2445 623/2.37 |
| 5,074,129 | A | 12/1991 | Matthew |
| 5,087,243 | A | 2/1992 | Avitall |
| 5,131,905 | A | 7/1992 | Grooters |
| 5,143,082 | A | 9/1992 | Kindberg et al. |
| 5,150,706 | A * | 9/1992 | Cox .................... A61F 7/10 128/897 |
| 5,186,711 | A | 2/1993 | Epstein |
| 5,188,813 | A | 2/1993 | Fairey et al. |
| 5,192,314 | A | 3/1993 | Daskalakis |
| 5,207,725 | A | 5/1993 | Pinkerton |
| 5,224,363 | A | 7/1993 | Sutton |
| 5,256,132 | A | 10/1993 | Snyders |
| 5,279,539 | A | 1/1994 | Bohan et al. |
| 5,290,217 | A | 3/1994 | Campos |
| 5,336,253 | A | 8/1994 | Gordon et al. |
| 5,339,657 | A | 8/1994 | McMurray |
| 5,341,815 | A | 8/1994 | Cofone et al. |
| 5,356,432 | A | 10/1994 | Rutkow et al. |
| 5,366,460 | A | 11/1994 | Eberbach |
| 5,383,840 | A | 1/1995 | Heilman et al. |
| 5,385,156 | A | 1/1995 | Oliva |
| 5,405,360 | A | 4/1995 | Tovey |
| 5,409,703 | A | 4/1995 | McAnalley et al. |
| 5,429,584 | A | 7/1995 | Chiu |
| 5,507,779 | A | 4/1996 | Altman |
| 5,524,633 | A | 6/1996 | Heaven et al. |
| 5,533,958 | A | 7/1996 | Wilk |
| 5,558,617 | A | 9/1996 | Heilman et al. |
| 5,571,088 | A | 11/1996 | Lennox et al. |
| 5,593,441 | A | 1/1997 | Lichtenstein et al. |
| 5,603,337 | A | 2/1997 | Jarvik |
| 5,611,515 | A | 3/1997 | Benderev et al. |
| 5,647,380 | A | 7/1997 | Campbell et al. |
| 5,695,525 | A | 12/1997 | Mulhauser et al. |
| 5,702,343 | A | 12/1997 | Alferness |
| 5,713,954 | A | 2/1998 | Rosenberg et al. |
| 5,735,290 | A | 4/1998 | Sterman et al. |
| 5,766,216 | A | 6/1998 | Gangal et al. |
| 5,782,746 | A | 7/1998 | Wright |
| D399,000 | S | 9/1998 | Rothman et al. |
| 5,800,334 | A | 9/1998 | Wilk |
| 5,800,528 | A | 9/1998 | Lederman et al. |
| 5,839,842 | A | 11/1998 | Wanat et al. |
| 5,848,962 | A | 12/1998 | Feindt |
| 5,853,422 | A | 12/1998 | Huebsch et al. |
| 5,928,250 | A | 7/1999 | Koike et al. |
| 5,931,810 | A | 8/1999 | Grabek |
| 5,961,440 | A | 10/1999 | Schweich, Jr. et al. |
| 5,972,013 | A | 10/1999 | Schmidt |
| 5,976,551 | A | 11/1999 | Mottez et al. |
| 5,990,378 | A | 11/1999 | Ellis |
| 6,042,536 | A | 3/2000 | Tihon et al. |
| 6,045,497 | A | 4/2000 | Schweich, Jr. et al. |
| 6,050,936 | A | 4/2000 | Schweich, Jr. et al. |
| 6,059,715 | A | 5/2000 | Schweich, Jr. et al. |
| 6,076,013 | A | 6/2000 | Brennan et al. |
| 6,077,214 | A | 6/2000 | Mortier et al. |
| 6,077,218 | A | 6/2000 | Alferness |
| 6,085,754 | A | 7/2000 | Alferness et al. |
| 6,089,051 | A | 7/2000 | Gorywoda et al. |
| 6,095,968 | A | 8/2000 | Snyders |
| 6,123,662 | A | 9/2000 | Alferness |
| 6,126,590 | A | 10/2000 | Alferness |
| 6,155,968 | A | 12/2000 | Wilk |
| 6,155,972 | A | 12/2000 | Nauertz et al. |
| 6,162,168 | A | 12/2000 | Schweich, Jr. et al. |
| 6,165,119 | A | 12/2000 | Schweich, Jr. et al. |
| 6,165,120 | A | 12/2000 | Schweich, Jr. et al. |
| 6,165,121 | A | 12/2000 | Alferness |
| 6,165,122 | A | 12/2000 | Alferness |
| 6,169,922 | B1 | 1/2001 | Alferness et al. |
| 6,174,279 | B1 | 1/2001 | Girard |
| 6,179,791 | B1 | 1/2001 | Krueger |
| 6,183,411 | B1 | 2/2001 | Mortier et al. |
| 6,190,408 | B1 | 2/2001 | Melvin |
| 6,193,646 | B1 | 2/2001 | Kulisz et al. |
| 6,193,648 | B1 | 2/2001 | Krueger |
| 6,205,747 | B1 | 3/2001 | Olaechea |
| 6,206,004 | B1 | 3/2001 | Schmidt et al. |
| 6,206,820 | B1 | 3/2001 | Kazi |
| 6,221,103 | B1 | 4/2001 | Melvin |
| 6,224,540 | B1 | 5/2001 | Lederman et al. |
| 6,230,714 | B1 | 5/2001 | Alferness et al. |
| 6,241,654 | B1 | 6/2001 | Alferness |
| 6,260,552 | B1 | 7/2001 | Mortier et al. |
| 6,261,222 | B1 | 7/2001 | Schweich, Jr. et al. |
| 6,264,602 | B1 | 7/2001 | Mortier et al. |
| 6,293,906 | B1 | 9/2001 | Vanden Hoek et al. |
| 6,332,863 | B1 | 12/2001 | Schweich, Jr. et al. |
| 6,332,864 | B1 | 12/2001 | Schweich, Jr. et al. |
| 6,332,893 | B1 | 12/2001 | Mortier et al. |
| 6,360,749 | B1 | 3/2002 | Jayaraman |
| 6,370,429 | B1 | 4/2002 | Alferness et al. |
| 6,375,608 | B1 | 4/2002 | Alferness |
| 6,402,679 | B1 | 6/2002 | Mortier |
| 6,402,680 | B2 | 6/2002 | Mortier |
| 6,406,420 | B1 | 6/2002 | McCarthy et al. |
| 6,409,760 | B1 | 6/2002 | Melvin |
| 6,416,459 | B1 | 7/2002 | Haindl |
| 6,416,554 | B1 | 7/2002 | Alferness et al. |
| 6,425,856 | B1 | 7/2002 | Shapland et al. |
| 6,432,039 | B1 | 8/2002 | Wardle |
| 6,482,146 | B1 | 11/2002 | Alferness et al. |
| 6,488,618 | B1 | 12/2002 | Paolitto et al. |
| 6,494,825 | B1 | 12/2002 | Talpade |
| 6,508,756 | B1 | 1/2003 | Kung et al. |
| 6,514,194 | B2 | 2/2003 | Schweich, Jr. et al. |
| 6,517,570 | B1 | 2/2003 | Lau et al. |
| 6,520,904 | B1 | 2/2003 | Melvin |
| 6,537,198 | B1 | 3/2003 | Vidlund et al. |
| 6,537,203 | B1 | 3/2003 | Alferness et al. |
| 6,541,678 | B2 | 4/2003 | Klein |

(56) References Cited

U.S. PATENT DOCUMENTS

| | | |
|---|---|---|
| 6,544,168 B2 | 4/2003 | Alferness |
| 6,547,716 B1 | 4/2003 | Milbocker |
| 6,558,319 B1 | 5/2003 | Aboul-Hosn et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi et al. |
| 6,589,160 B2 | 7/2003 | Schweich, Jr. et al. |
| 6,592,514 B2 | 7/2003 | Kolata et al. |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,620,095 B2 | 9/2003 | Taheri |
| 6,622,730 B2 | 9/2003 | Ekvall et al. |
| 6,629,921 B1 | 10/2003 | Schweich, Jr. et al. |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,627 B2 | 2/2004 | Jayaraman |
| 6,685,628 B2 | 2/2004 | Dinh |
| 6,689,048 B2 | 2/2004 | Vanden Hoek et al. |
| 6,695,768 B1 | 2/2004 | Levine et al. |
| 6,695,769 B2 | 2/2004 | French et al. |
| 6,701,929 B2 | 2/2004 | Hussein |
| 6,702,732 B1 | 3/2004 | Lau et al. |
| 6,709,382 B1 | 3/2004 | Horner |
| 6,716,158 B2 | 4/2004 | Raman |
| 6,723,038 B1 | 4/2004 | Schroeder et al. |
| 6,723,041 B2 | 4/2004 | Lau et al. |
| 6,726,696 B1 | 4/2004 | Houser et al. |
| 6,726,920 B1 | 4/2004 | Theeuwes et al. |
| 6,727,316 B1 | 4/2004 | Bremser |
| 6,730,016 B1 | 5/2004 | Cox et al. |
| 6,746,471 B2 | 6/2004 | Mortier et al. |
| 6,755,777 B2 | 6/2004 | Schweich, Jr. et al. |
| 6,755,779 B2 | 6/2004 | Vanden Hoek et al. |
| 6,755,861 B2 | 6/2004 | Nakao |
| 6,764,510 B2 | 7/2004 | Vidlund et al. |
| 6,776,754 B1 | 8/2004 | Wilk |
| 6,793,618 B2 | 9/2004 | Schweich, Jr. et al. |
| 6,808,488 B2 | 10/2004 | Mortier et al. |
| 6,852,075 B1 | 2/2005 | Taylor |
| 6,852,076 B2 | 2/2005 | Nikolic et al. |
| 6,858,001 B1 | 2/2005 | Aboul-Hosn |
| 6,876,887 B2 | 4/2005 | Okuzumi et al. |
| 6,881,185 B2 | 4/2005 | Vanden Hoek et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 6,918,870 B1 | 7/2005 | Hunyor et al. |
| 6,951,534 B2 | 10/2005 | Girard et al. |
| 6,997,865 B2 | 2/2006 | Alferness et al. |
| 7,022,063 B2 | 4/2006 | Lau et al. |
| 7,022,064 B2 | 4/2006 | Alferness et al. |
| 7,025,719 B2 | 4/2006 | Alferness et al. |
| 7,060,023 B2 | 6/2006 | French et al. |
| 7,077,862 B2 | 7/2006 | Vidlund et al. |
| 7,081,086 B2 | 7/2006 | Lau et al. |
| 7,112,219 B2 | 9/2006 | Vidlund |
| 7,155,295 B2 | 12/2006 | Lau et al. |
| 7,163,507 B2 | 1/2007 | Alferness et al. |
| 7,181,272 B2 | 2/2007 | Struble et al. |
| 7,189,203 B2 | 3/2007 | Lau et al. |
| 7,214,180 B2 | 5/2007 | Chin |
| 7,235,042 B2 | 6/2007 | Vanden Hoek et al. |
| 7,252,632 B2 | 8/2007 | Shapland et al. |
| 7,276,022 B2 | 10/2007 | Lau et al. |
| 7,291,105 B2 | 11/2007 | Lau et al. |
| 7,297,104 B2 | 11/2007 | Vanden Hoek et al. |
| 7,351,200 B2 | 4/2008 | Alferness |
| 7,354,396 B2 | 4/2008 | French et al. |
| 7,361,139 B2 | 4/2008 | Lau et al. |
| 7,366,659 B2 | 4/2008 | Etter |
| 7,390,293 B2 | 6/2008 | Jayaraman |
| 7,398,781 B1 | 7/2008 | Chin |
| 7,404,793 B2 | 7/2008 | Lau |
| 7,404,973 B2 | 7/2008 | Lau et al. |
| 7,410,461 B2 | 8/2008 | Lau et al. |
| 7,468,029 B1 | 12/2008 | Robertson |
| 7,621,866 B2 | 11/2009 | Dietz et al. |
| 7,651,462 B2 | 1/2010 | Hjelle et al. |
| 7,736,299 B2 | 6/2010 | Klenk et al. |
| 7,955,247 B2 | 6/2011 | Levine et al. |
| 8,092,363 B2 | 1/2012 | Leinsing et al. |
| 8,100,821 B2 | 1/2012 | Hjelle et al. |
| 8,109,868 B2 | 2/2012 | Girard et al. |
| 8,202,212 B2 | 6/2012 | Hjelle et al. |
| 8,277,372 B2 | 10/2012 | Alferness et al. |
| 8,617,051 B2 | 12/2013 | Hjelle et al. |
| 2001/0016675 A1 | 8/2001 | Monier et al. |
| 2001/0025171 A1 | 9/2001 | Monier et al. |
| 2002/0019580 A1 | 2/2002 | Lau et al. |
| 2002/0029080 A1 | 3/2002 | Mortier et al. |
| 2002/0045798 A1 | 4/2002 | Lau et al. |
| 2002/0058855 A1 | 5/2002 | Schweich, Jr. et al. |
| 2002/0068849 A1 | 6/2002 | Schweich, Jr. et al. |
| 2002/0068850 A1 | 6/2002 | Vanden Hoek et al. |
| 2002/0077524 A1 | 6/2002 | Schweich, Jr. et al. |
| 2002/0091296 A1 | 7/2002 | Alferness |
| 2002/0133055 A1 | 9/2002 | Handl |
| 2002/0147406 A1 | 10/2002 | Von Segesser |
| 2002/0151766 A1* | 10/2002 | Shapland ............... A61F 2/2481 600/37 |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0173694 A1 | 11/2002 | Mortier et al. |
| 2003/0032979 A1 | 2/2003 | Mortier et al. |
| 2003/0050529 A1 | 3/2003 | Vidlund et al. |
| 2003/0060895 A1 | 3/2003 | French et al. |
| 2003/0065248 A1 | 4/2003 | Lau et al. |
| 2003/0088149 A1 | 5/2003 | Raman et al. |
| 2003/0130731 A1 | 7/2003 | Vidlund et al. |
| 2003/0166992 A1 | 9/2003 | Schweich, Jr. et al. |
| 2003/0171641 A1 | 9/2003 | Schweich, Jr. et al. |
| 2003/0181928 A1 | 9/2003 | Vidlund et al. |
| 2003/0216611 A1* | 11/2003 | Vu ................... A61B 17/00234 600/37 |
| 2003/0229260 A1 | 12/2003 | Girard et al. |
| 2003/0229265 A1 | 12/2003 | Girard et al. |
| 2003/0233023 A1 | 12/2003 | Khaghani et al. |
| 2004/0002626 A1 | 1/2004 | Feld et al. |
| 2004/0010180 A1 | 1/2004 | Scorvo |
| 2004/0034272 A1 | 2/2004 | Diaz et al. |
| 2004/0059181 A1 | 3/2004 | Alferness |
| 2004/0064014 A1 | 4/2004 | Melvin et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0147805 A1 | 7/2004 | Lau et al. |
| 2004/0147965 A1 | 7/2004 | Berger |
| 2004/0158123 A1* | 8/2004 | Jayaraman ....... A61B 17/00234 600/37 |
| 2004/0167374 A1 | 8/2004 | Schweich et al. |
| 2004/0181118 A1 | 9/2004 | Kochamba |
| 2004/0181120 A1 | 9/2004 | Kochamba |
| 2004/0181124 A1 | 9/2004 | Alferness |
| 2004/0186342 A1 | 9/2004 | Vanden Hock et al. |
| 2004/0210104 A1 | 10/2004 | Lau et al. |
| 2004/0215308 A1 | 10/2004 | Bardy et al. |
| 2004/0225304 A1 | 11/2004 | Vidlund et al. |
| 2004/0243229 A1 | 12/2004 | Vidlund et al. |

(56) References Cited

U.S. PATENT DOCUMENTS

| | | |
|---|---|---|
| 2004/0249242 A1 | 12/2004 | Lau et al. |
| 2004/0267083 A1 | 12/2004 | McCarthy et al. |
| 2004/0267329 A1 | 12/2004 | Raman et al. |
| 2005/0004428 A1 | 1/2005 | Cox et al. |
| 2005/0010079 A1 | 1/2005 | Bertolero et al. |
| 2005/0014992 A1 | 1/2005 | Lilip et al. |
| 2005/0020874 A1 | 1/2005 | Lau et al. |
| 2005/0033109 A1 | 2/2005 | Lau et al. |
| 2005/0038316 A1 | 2/2005 | Taylor |
| 2005/0054892 A1 | 3/2005 | Lau et al. |
| 2005/0059853 A9 | 3/2005 | Kochambe |
| 2005/0059854 A1 | 3/2005 | Hoek et al. |
| 2005/0059855 A1 | 3/2005 | Lau et al. |
| 2005/0065396 A1 | 3/2005 | Mortier et al. |
| 2005/0075723 A1 | 4/2005 | Schroeder et al. |
| 2005/0085688 A1 | 4/2005 | Girard et al. |
| 2005/0090707 A1 | 4/2005 | Lau et al. |
| 2005/0133941 A1 | 6/2005 | Schuhmacher |
| 2005/0143620 A1 | 6/2005 | Mortier et al. |
| 2005/0148814 A1 | 7/2005 | Fischi et al. |
| 2005/0171589 A1 | 8/2005 | Lau et al. |
| 2005/0192474 A1 | 9/2005 | Vanden Hoek et al. |
| 2005/0197527 A1 | 9/2005 | Bolling |
| 2005/0228217 A1 | 10/2005 | Alferness et al. |
| 2005/0256368 A1 | 11/2005 | Klenk et al. |
| 2005/0283042 A1 | 12/2005 | Meyer et al. |
| 2005/0288715 A1 | 12/2005 | Lau et al. |
| 2006/0004249 A1 | 1/2006 | Kute et al. |
| 2006/0009675 A1 | 1/2006 | Meyer |
| 2006/0009831 A1 | 1/2006 | Lau et al. |
| 2006/0052660 A1* | 3/2006 | Chin ............... A61B 17/00008 600/37 |
| 2006/0063970 A1 | 3/2006 | Raman et al. |
| 2006/0155165 A1 | 7/2006 | Vanden Hoek et al. |
| 2006/0229490 A1 | 10/2006 | Chin |
| 2006/0241748 A1* | 10/2006 | Lee ....................... A61F 2/2466 623/2.37 |
| 2006/0270896 A1 | 11/2006 | Dietz et al. |
| 2007/0032696 A1 | 2/2007 | Duong |
| 2007/0043416 A1 | 2/2007 | Callas et al. |
| 2007/0208211 A1 | 9/2007 | Alferness et al. |
| 2007/0208215 A1 | 9/2007 | Hjelle |
| 2007/0208217 A1 | 9/2007 | Walsh et al. |
| 2007/0219407 A1 | 9/2007 | Vanden Hoek et al. |
| 2007/0225547 A1 | 9/2007 | Alferness et al. |
| 2007/0255093 A1 | 11/2007 | Lau et al. |
| 2008/0033234 A1 | 2/2008 | Hjelle et al. |
| 2008/0064917 A1 | 3/2008 | Bar et al. |
| 2009/0062596 A1 | 3/2009 | Leinsing et al. |
| 2009/0131743 A1 | 5/2009 | Hjelle et al. |
| 2010/0004504 A1 | 1/2010 | Callas |
| 2010/0094080 A1 | 4/2010 | Hjelle et al. |
| 2010/0160721 A1 | 6/2010 | Alferness et al. |
| 2010/0185050 A1 | 7/2010 | Alferness et al. |
| 2010/0268019 A1 | 10/2010 | Hjelle et al. |
| 2011/0015616 A1 | 1/2011 | Straubinger et al. |
| 2012/0253112 A1 | 10/2012 | Hjelle et al. |
| 2014/0181124 A1 | 6/2014 | Hofmeier et al. |

FOREIGN PATENT DOCUMENTS

| | | |
|---|---|---|
| DE | 29517393 | 2/1996 |
| EP | 0280564 | 8/1988 |
| EP | 0303719 | 2/1989 |
| EP | 0557964 | 9/1993 |
| GB | 2209678 | 5/1989 |
| JP | 60-203250 | 10/1985 |
| JP | 01-145066 | 6/1989 |
| JP | 02-271829 | 11/1990 |
| JP | 2002-532189 | 10/2002 |
| SU | 1009457 | 4/1983 |
| WO | WO 1993/03685 | 3/1993 |
| WO | WO 1996/16601 | 6/1996 |
| WO | WO 1996/31175 | 10/1996 |
| WO | WO 1998/14136 | 4/1998 |
| WO | WO 1998/29041 | 7/1998 |
| WO | WO 1998/35632 | 8/1998 |
| WO | WO 1998/58598 | 12/1998 |
| WO | WO 1999/44534 | 9/1999 |
| WO | WO 1999/52470 | 10/1999 |
| WO | WO 1999/52471 | 10/1999 |
| WO | WO 2000/01306 | 1/2000 |
| WO | WO 2000/02500 | 1/2000 |
| WO | WO 2000/06026 | 2/2000 |
| WO | WO 2000/06027 | 2/2000 |
| WO | WO 2000/06028 | 2/2000 |
| WO | WO 2000/16700 | 3/2000 |
| WO | WO 2000/28912 | 5/2000 |
| WO | WO 2000/28918 | 5/2000 |
| WO | WO 00/36995 | 6/2000 |
| WO | WO 2001/02500 | 1/2001 |
| WO | WO 2001/03608 | 1/2001 |
| WO | WO 2001/10421 | 2/2001 |
| WO | WO 2001/67985 | 9/2001 |
| WO | WO 2001/91667 | 12/2001 |
| WO | WO 2001/95830 | 12/2001 |
| WO | WO 2002/13726 | 2/2002 |
| WO | WO 2002/000099 | 9/2002 |
| WO | WO 2003/022131 | 3/2003 |
| WO | WO 2006/023580 | 3/2006 |
| WO | WO 2008/011411 | 1/2008 |
| WO | WO 2010/111592 | 9/2010 |

OTHER PUBLICATIONS

U.S. Appl. No. 14/053,261, filed Oct. 2013, Hjelle et al.
U.S. Appl. No. 14/053,587, filed Oct. 2013, Hjelle et al.
U.S. Appl. No. 14/053,590, filed Oct. 2013, Hjelle et al.
U.S. Appl. No. 29/469,753, filed Oct. 2013, Hjelle et al.
U.S. Appl. No. 60/148,130, filed Aug. 1999, Chin.
U.S. Appl. No. 60/150,737, filed Aug. 1999, Chin.
"Abstracts From the 68th Scientific Sessions, Anaheim Convention Center, Anaheim, California, Nov. 13-16, 1995," American Heart Association Supplement to Circulation, vol. 92, No. 8, Abstracts 1810-1813 (Oct. 15, 1995).
Bolling, et al., "Intermediate-Term Outcome of Mitral Reconstruction in Cardiomyopathy", J Thorac. Cardiovasc. Surg., Feb. 1998, 115(2):381-388.
Bourge, "Clinical Trial Begins for Innovative Device-Altering Left Ventricular Shape in Heart Failure", UAB Insight, posted Aug. 8, 2012, retrieved Jun. 17, 2004 , http://www.health.uab.edu/show, 2 pages.
Capomolla et al., "Dobutamine and nitroprusside infusion in patients with severe congestive heart failure: Hemodynamic improvement by discordant effects on mitral regurgitation, left atrial function, and ventricular function", American Heart Journal, Dec. 1997, 1089-1098.
Capouya et al., "Girdling Effect of Nonstimulated Cardiomyoplasty on Left Ventricular Function", Ann Thorac. Surg., 1993, 56:867-871.
Cohn, "The Management of Chronic Heart Failure", *The New England Journal of Medicine*, Aug. 15, 1996, 335(7): 490-498.
Coletta et al., "Prognostic value of left ventricular vol. response during dobutamine stress echocardiography," *European Heart Journal*, Oct. 1997, 18: 1599-1605.
Daubeney et al., "Pulmonary Atresia/Intact Ventricular Septum: Early Outcome After Right Ventricular Outflow Reconstruction by Surgery or Catheter Intervention," Supplement to Circulation, Oct. 15, 1995, 92(8), Abstract 1812.
DeVries et al., "A Novel Technique for Measurement of Pericardial Balloon," *Am. J Physiol Heart Circ Physiol*, Jan. 2001, 280(6):H2815-H2822.
European Search Report in European Application No. 13844676.0, dated Jun. 2, 2016, 8 pages.
Extended European Search Report in European Application No. 13845313.9, dated Jun. 1, 2016, 8 pages.
Ghanta, et al., "Cardiovascular Surgery: Adjustable, Physiological Ventricular Restraint Improves Left Ventricular Mechanics and Reduces Dilation in an Ovine Model of Chronic Heart Failure," *Circulation, JAHA*, 2007, 115:1201-10.

(56) References Cited

OTHER PUBLICATIONS

Guasp., "Una protesis contentiva para el tratamiento de la miocardiopatia dilatada," *Revista Espanola de Cardiologia*, Jul. 1998, 51(7): 521-528.

Hamilton et al., "Static and Dynamic Operating Characteristics of a Pericardial Balloon," *J Appl. Physiol*, Apr. 2001, 90(4):1481-1488.

Hung, et al., "Persistent Reduction of Ischemic Mitral Regurgitation by Papillary Muscle Repositioning: Structural Stabilization of the Pipillary Muscle Ventricular Wall Complex," *Circulation, JAHA*, 2007, 116:1-259 1-263.

International Search Report and Written Opinion in International Application No. PCT/US2013/064894, dated Apr. 3, 2014, 27 pages.

International Search Report and Written Opinion in International Application No. PCT/US2013/064895, dated Apr. 21, 2014, 14 pages.

Justo et al., "Outcomes of Transcatheter Perforation of the Right Ventricular Outflow Tract as Primary Management for Pulmonary Valve Atresia in the Newborn," Supplement to Circulation, Oct. 15, 1995, 92(8), Abstract 1813.

Kass et al., "Reverse Remodeling From Cardiomyoplasty in Human Heart Failure External Constraint Versus Active Assist," *Circulation*, May 1, 1995, 91(9):2314-2318, retrieved Jan. 16, 2014, http://circ.ahajournals.org/content/91/9/2314.full.

Labrousse, Louis et al., "Implantation of a Cardiac Support Device by the 'Parachute-Like' Technique Through Sternal and Trans-Abdominal Approach," Abstract, *94 Programme of the 4th EACTSIESTS Joint Meeting*, Sep. 28, 2005, Barcelona, Spain.

Lamas, et al., "Clinical Significance of Mitral Regurgitation After Acute Myocardial Infarction," Circulation—JAHA, Aug. 5, 1997, 96(3):827-833, retrieved Jan. 16, 2014, http://circ.ahajournals.org/content/96/3/827.long.

Lei-Cohen, et al., "Design of a New Surgical Approach for Ventricular Remodeling to Relieve Ischemic Mitral Regurgitation," *Circulation*, Jun. 13, 2000, 101:2756-2763.

Levin et al., "Reversal of Chronic Ventricular Dilation in Patients with End-Stage Cardiomyopathy by Prolonged Mechanical Unloading," *Circulation*, Jun. 1, 1995, 91(11): 2717-2720, retrieved Jan. 16, 2014, http://circ.ahajournals.org/content/91/11/2717.long.

Lloyd et al., "The PDA Coil Registry: Report of the First 535 Procedures," Supplement to Circulation, Oct. 15, 1995, 92(8), Abstract 1811.

Oh et al., "The Effects of Prosthetic Cardiac Binding and Adynamic Cardiomyoplasty in a Model of Dilated Cardiomyopathy," The Journal of Thoracic and Cardiovascular Surgery, Jul. 1998, 116(1):148-153.

Pai, et al., "Valvular Egurgitation," *Clinical Science Abstracts*, 2000, 1800-1804.

Paling, "Two-Bar Fabrics (Part-Set Threading)", *Warp Knitting Technology*, Columbine Press (Publishers) Ltd., Buxton, Great Britain, p. III (1970).

Timek, et al., "Pathogenesis of Mitral Regurgitation in Tachycardia Induced Cardiomyopathy," Circulation—JAHA, 2001, 104:1-47-I-53.

Vaynblat et al., "Cardiac Binding in Experimental Heart Failure," *Ann. Thorac. Surg.*, 1994, vol. 64, 11 pages.

Vinereanu, et al., "'Pure' diastolic dysfunction is associated with long-axis systolic dysfunction. Implications for the diagnosis and classification of heart failure," *European Journal of Heart Failure*, Aug. 2005, 7(5): 820-828 (Abstract Only).

\* cited by examiner

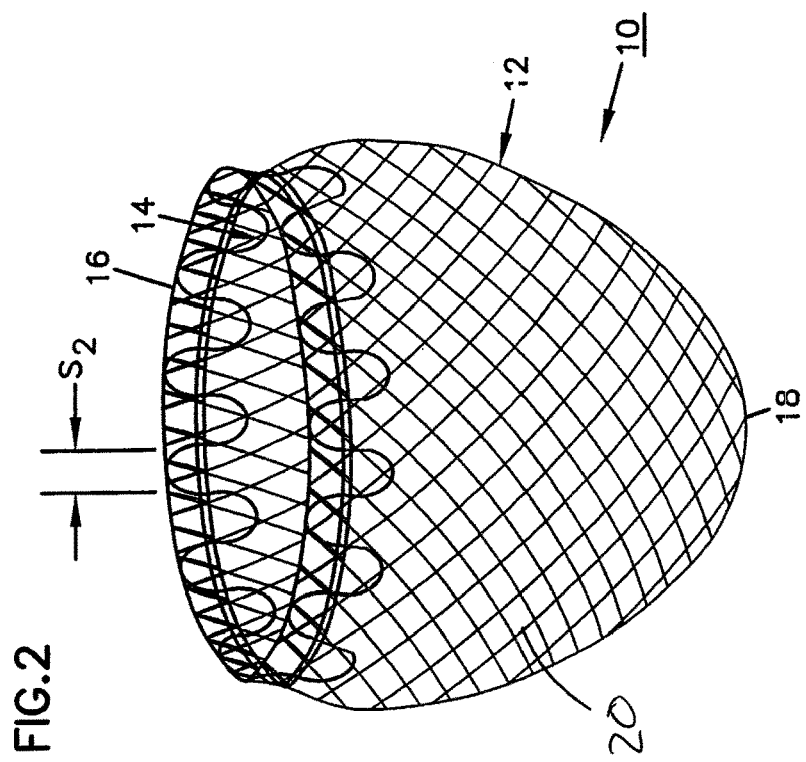
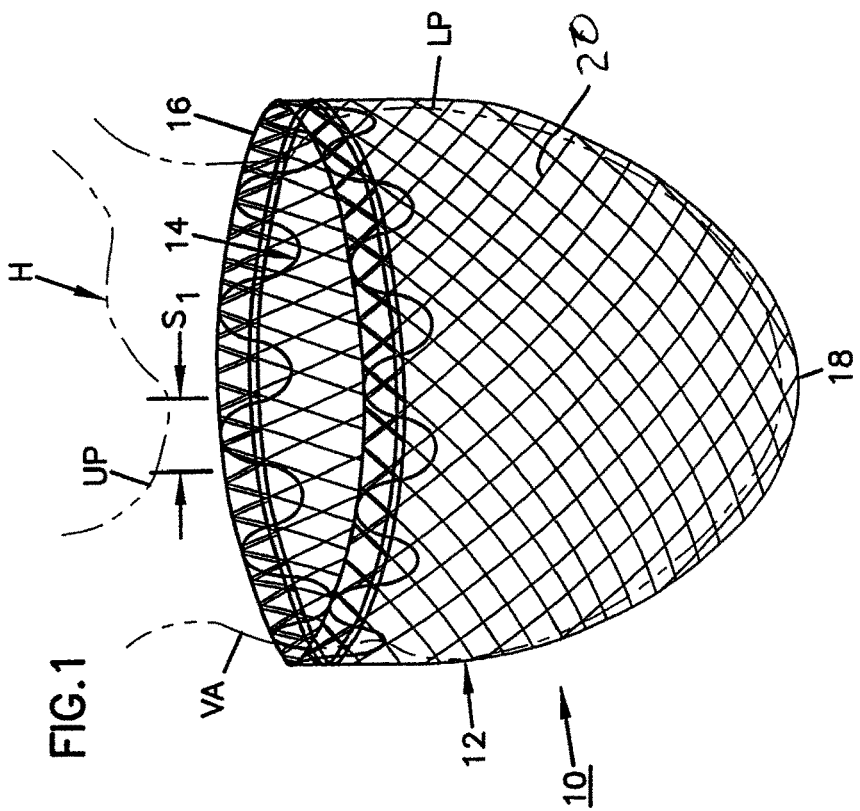

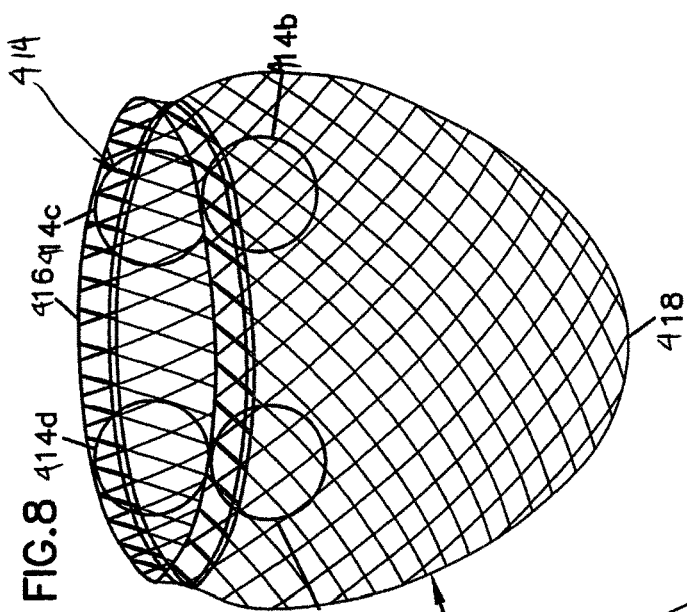
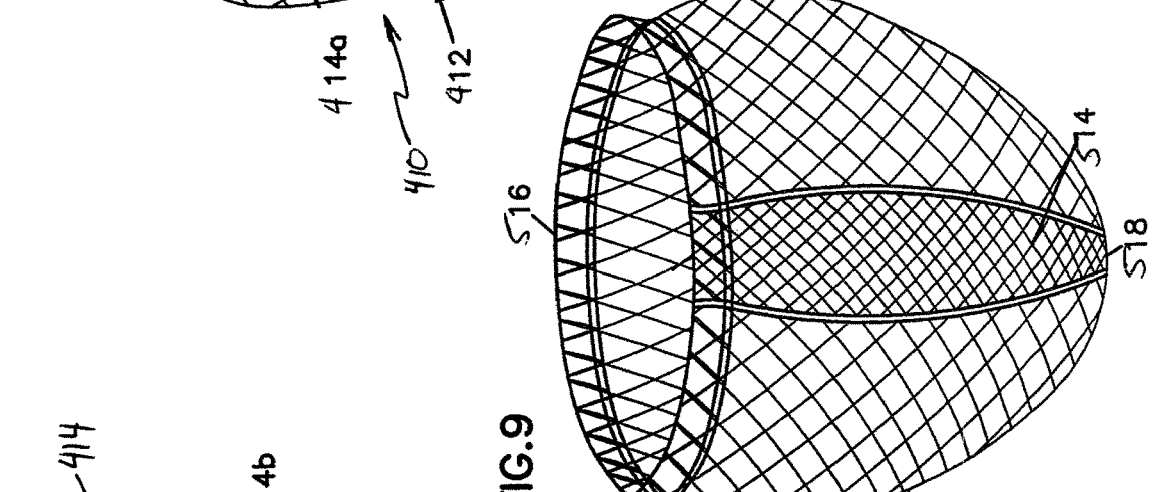
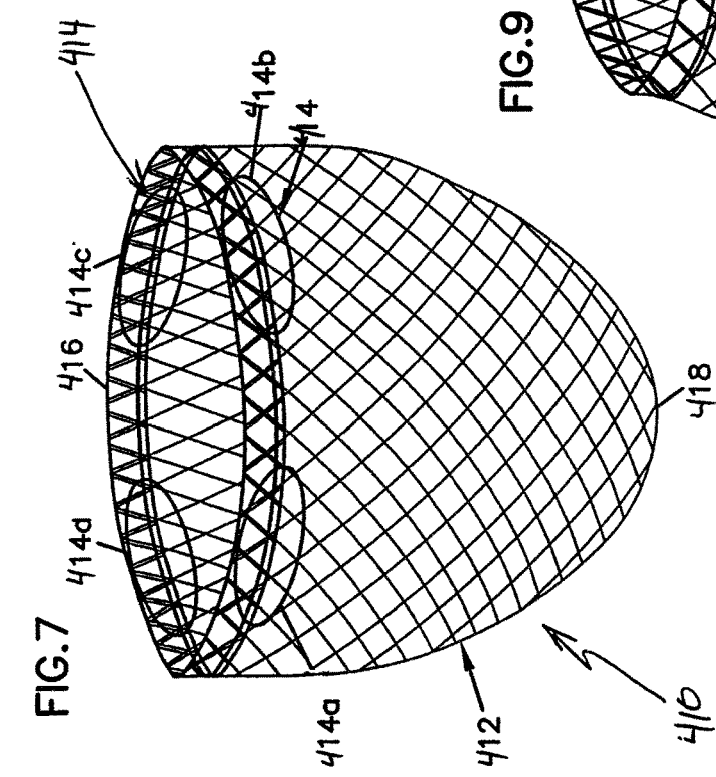

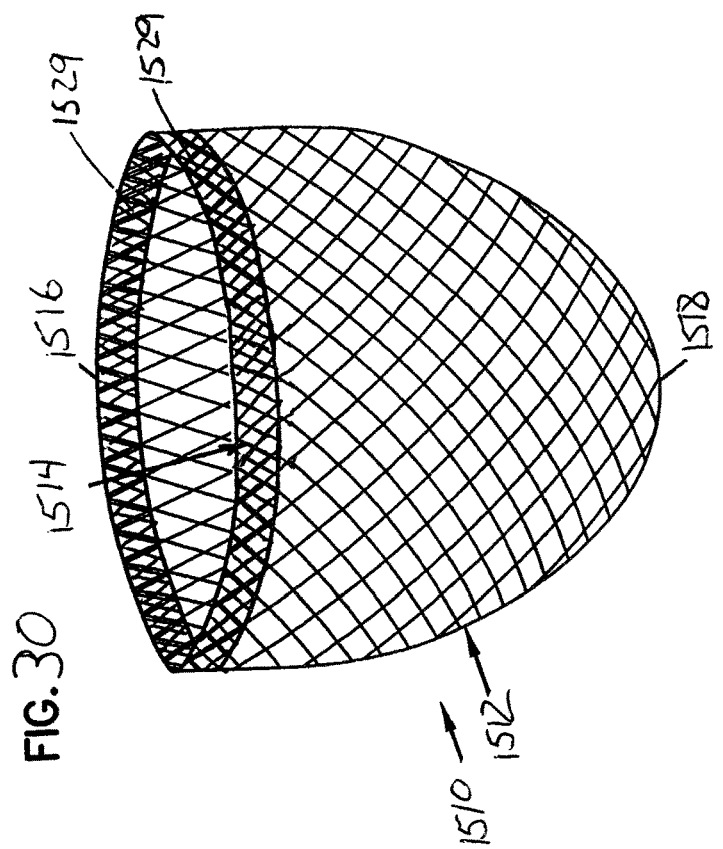
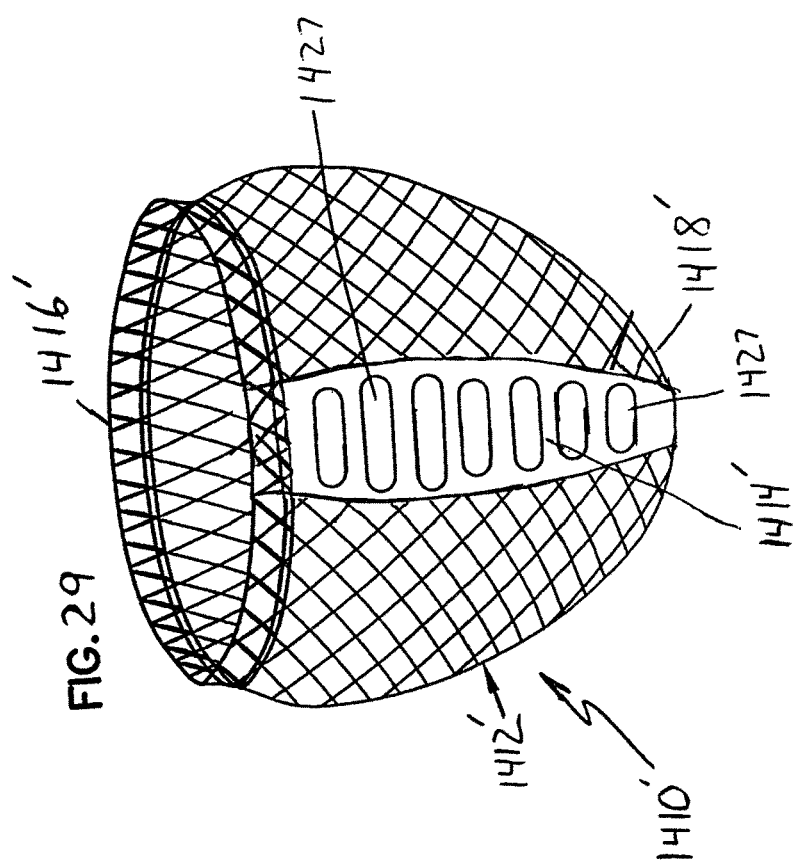

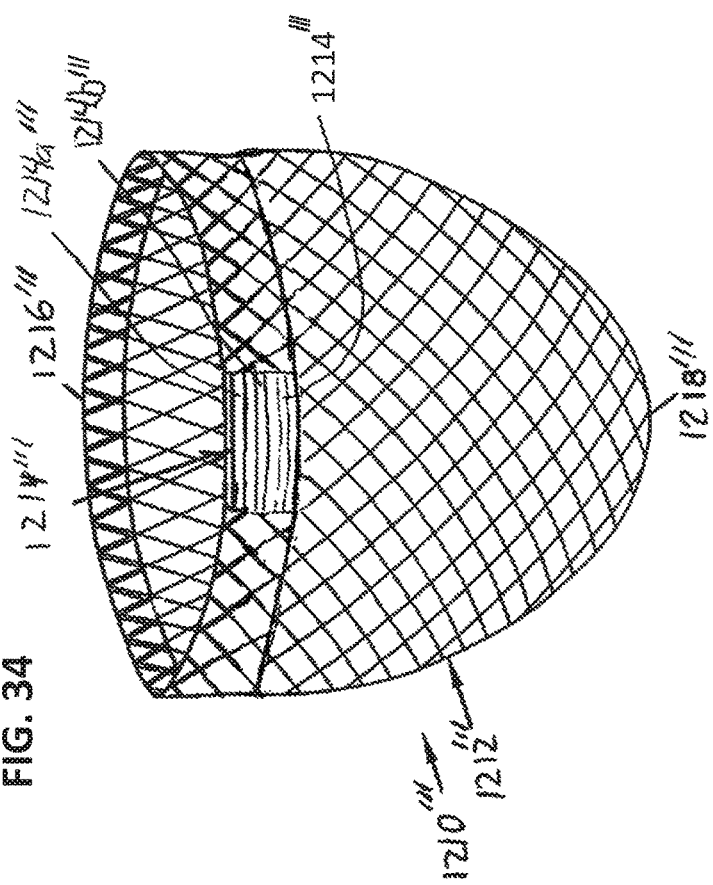
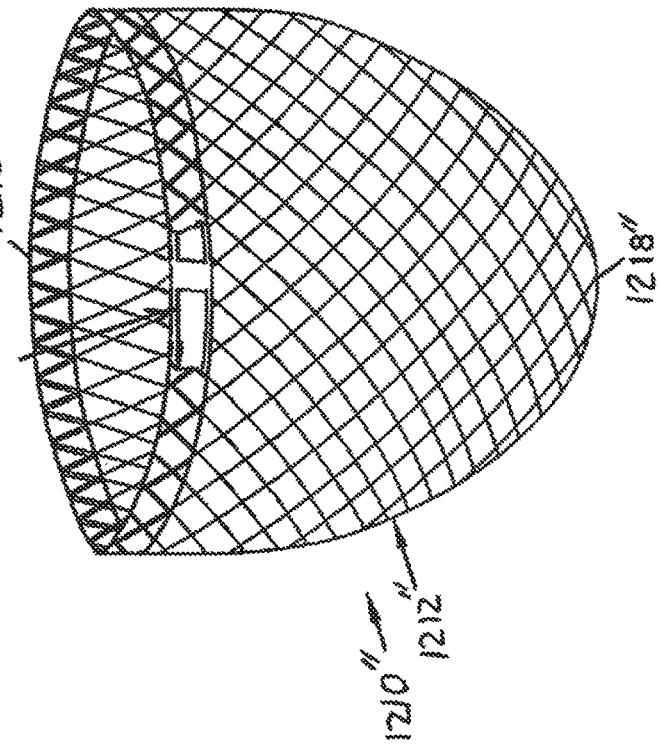

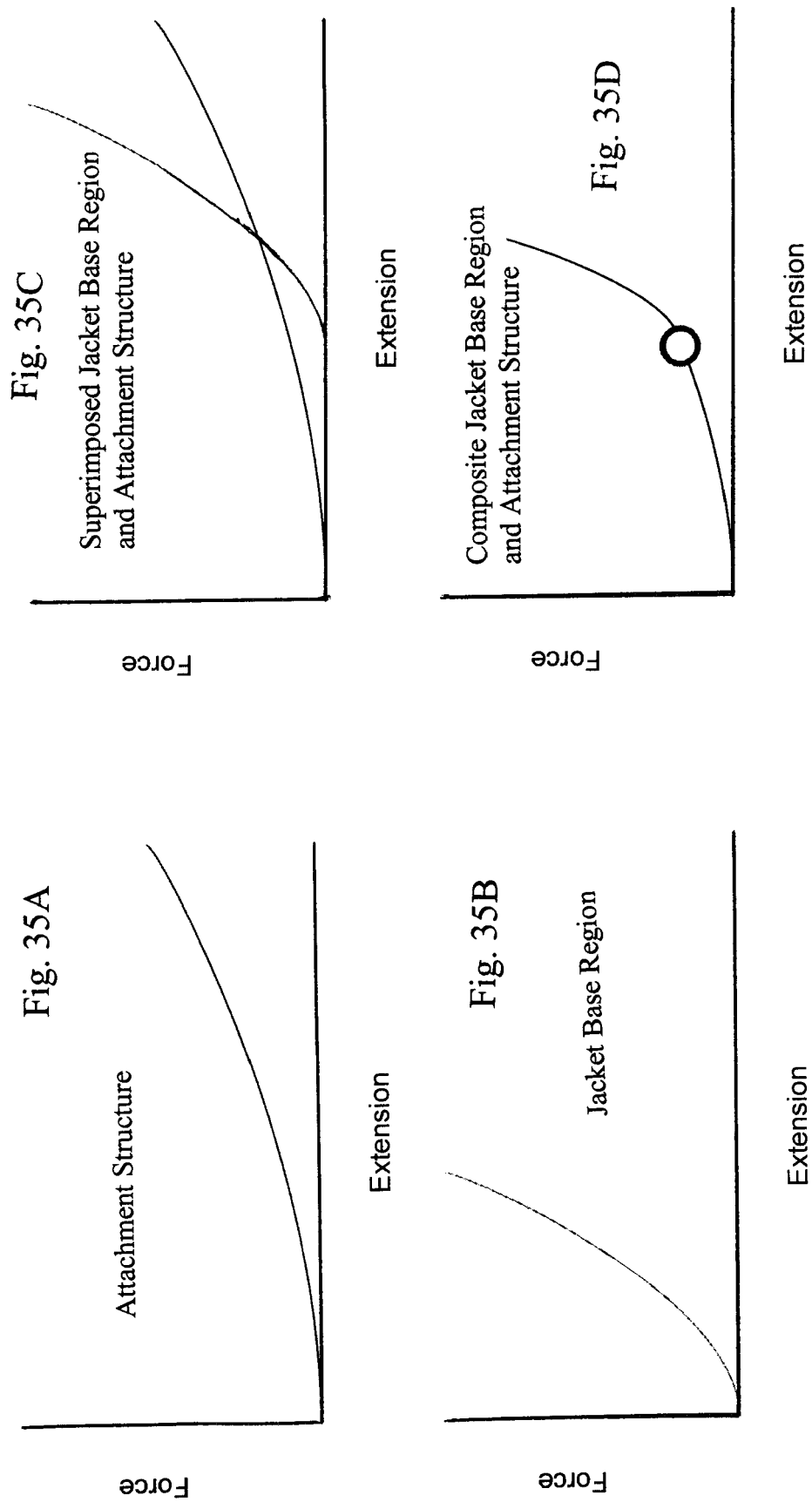

SELF-ADJUSTING ATTACHMENT STRUCTURE FOR A CARDIAC SUPPORT DEVICE

CROSS-REFERENCE TO RELATED APPLICATION

This application is a continuation of U.S. patent application Ser. No. 13/048,588, filed Mar. 15, 2011, now U.S. Pat. No. 9,737,403, which is a continuation of U.S. patent application Ser. No. 12/701,302, filed Feb. 5, 2010, now abandoned, which is a continuation of U.S. patent application Ser. No. 11/368,257, filed Mar. 3, 2006, now abandoned. The prior applications are hereby incorporated herein by reference in their entirety and for all purposes.

FIELD OF THE INVENTION

The invention relates to devices for providing wall tension relief for a diseased heart. In particular, this invention pertains to such a device which is self-adjusting after placement on the heart.

BACKGROUND OF THE INVENTION

Congestive heart disease is a progressive and debilitating illness. The disease is characterized by a progressive enlargement of the heart. As the heart enlarges, the heart is performing an increasing amount of work in order to pump blood during each heartbeat. In time, the heart becomes so enlarged that it cannot adequately supply blood. An afflicted patient is fatigued, unable to perform even simple exerting tasks and experiences pain and discomfort. Furthermore, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is a commonly proscribed treatment. Drug therapy treats the symptoms of the disease and may slow the progression of the disease. However, even with drug therapy, the disease will typically progress. Furthermore, the drugs sometimes have adverse side effects.

One relatively permanent treatment for congestive heart disease is heart transplant. To qualify, a patient must be in the later stages of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients often suffer before qualifying for heart transplant. Furthermore, after this suffering, the available treatment is often unsatisfactory. Heart transplant procedures are risky, invasive and relatively expensive, and often extend a patient's life by only relatively short times. For example, prior to transplant, a Class IV patient may have a life expectancy of six months to one-year. Heart transplant can improve the expectancy to about five years. Unfortunately, not enough hearts are available for transplant to meet the needs of congestive heart disease patients. In the United States, in excess of 35,000 transplant candidates compete for only about 2,000 transplants per year. A transplant waiting list can be about eight to twelve months long on average and frequently a patient may have to wait about one to two years for a donor heart. Even if the risks and expense of heart transplant could be tolerated, this treatment option is becoming increasingly unavailable. Furthermore, many patients do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 550,000 new patients in the United States each year). Economic costs of the disease have been estimated at $38 billion annually.

Substantial efforts have been made to find alternative treatments for congestive heart disease. A surgical procedure referred to as the Batista procedure includes dissecting and removing portions of the heart in order to reduce heart volume. This procedure is the subject of some controversy. It is highly invasive, risky and relatively expensive and commonly includes other relatively expensive procedures (such as a concurrent heart valve replacement). Also, the treatment is limited to Class IV patients and, accordingly, provides limited hope to patients facing ineffective drug treatment prior to Class IV. Furthermore, the consequences of a failure of this procedure can be severe.

There is, therefore, a need for alternative treatments applicable to either or both the early and later stages of congestive heart disease to either stop or slow the progressive nature of the disease. Cardiomyoplasty is a treatment for relatively early stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has produced symptomatic improvement, the nature of the improvement is not fully understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 Circulation 2314-2318 (1995).

Even though cardiomyoplasty has demonstrated symptomatic improvement, at least some studies suggest the procedure only minimally improves cardiac performance. The procedure is invasive, requiring harvesting a patient's muscle and an open chest approach (i.e., sternotomy) to access the heart. The procedure is also complicated. For example, it is sometimes difficult to adequately wrap the muscle around the heart with a satisfactory fit. Also, if adequate blood flow is not maintained to the wrapped muscle, the muscle may necrose. The muscle may stretch after wrapping, thereby reducing its constraining benefits, and is generally not susceptible to post-operative adjustment. In addition, the muscle may fibrose and adhere to the heart causing undesirable constraint on the contraction of the heart during systole.

Mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. An example of a device of this type is shown in the Arnold U.S. Pat. No. 4,995,857. TAH devices, such as the known Jarvik heart, are used as temporary measures while a patient awaits a donor heart for transplant.

Other cardiac assist devices are disclosed in the Lundback U.S. Pat. No. 4,957,477, Grooters U.S. Pat. No. 5,131,905 and Snyders U.S. Pat. No. 5,256,132. Both the Grooters and Snyders patents disclose cardiac assist devices which pump fluid into chambers opposing the heart to assist systolic contractions of the heart. The Lundback patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber.

The commonly assigned Alferness U.S. Pat. No. 5,702,343 discloses a cardiac support device, sometimes referred to as a jacket, that constrains cardiac expansion to treat congestive heart disease and associated valvular dysfunction. One embodiment of the jacket is formed of a knit material of polyester having specific compliance and other material characteristics (including elasticity) more fully described in the Alferness et al. U.S. Pat. No. 6,482,146. Another embodiment of the jacket has a base end with a hem material of double layers as described in the Nauertz et al. U.S. Pat. No. 6,155,972.

Jackets of the types described in the Alferness et al. U.S. Pat. No. 6,482,146 and Nauertz et al. U.S. Pat. No. 6,155,972 have been demonstrated to be capable of providing effective treatment for congestive heart failure in certain patients. Surgical procedures for placing the jacket on a diseased heart include a full sternotomy in which the sternum or breast bone of the patient is cut and separated to provide an open-field access to the heart. During such an open procedure, a surgeon has direct visualization and a wide field of access to the heart. The base end of the jacket is opened and placed over the apex of the heart with the base end advanced to the atrial-ventricular groove (A-V groove). The surgeon can then secure the base end in the desired position through sutures or the like. It is noted in the Alferness U.S. Pat. No. 5,702,343 that other suitable securing arrangements include a circumferential attachment device such as a cord, suture, band, adhesive or shape memory element which passes around the circumference of the base of the jacket. The ends of the attachment device can be fastened together to secure the jacket in place.

Also, the surgeon can adjust the jacket on the heart by gathering any excess material and suturing the excess material together to get a desired amount of tension of the jacket on the heart. The Alfemess U.S. Pat. No. 5,702,343 also describes an alternative approach in which the jacket includes a mechanism for selectively adjusting the volumetric size of the jacket. A slot that opens on the base of the jacket and extends toward the apex end is described as one mechanism for providing the size adjusting function. Adjustment mechanisms are also disclosed in the Shapland et al. U.S. Pat. No. 6,425,856 and the Kung et al. U.S. Pat. No. 6,508,756. Other cardiac support devices are disclosed in Lau et al. U.S. Pat. Nos. 6,595,912 and 6,612,978.

While the open-chest implantation procedure is acceptable, it is desirable to be able to place a jacket on the heart through laparoscopic or other less-invasive procedures. During less-invasive procedures, the surgeon may have more limited access to the heart and more limited ability to ensure placement and alignment of a jacket on the heart. Properly placing and securing the jacket on the heart during minimally-invasive delivery procedures of these types can be more difficult than in open-chest procedures.

There is, therefore, a continuing need for improved structures for securing jackets or other cardiac support devices to the heart. In particular, there is a need for improved structures for attaching and fitting the devices to the heart. Structures of these types that are self-adjusting would be especially desirable. The structures should be capable of providing the attaching and/or fitting functions without interfering with the therapeutic functions of cardiac support devices. Structures that meet these objectives and can be used in connection with minimally-invasive delivery procedures would also be desirable.

SUMMARY OF THE INVENTION

The present invention is an improved cardiac support device. The device includes a jacket having a base region for constraining cardiac expansion. Attachment structure on a base region of the jacket self-secures the jacket to a heart. The attachment structure is an elastic structure. Examples of the attachment structure include undulating metal and polymer elements, a silicone band and elastomeric threads.

BRIEF DESCRIPTION OF THE DRAWINGS

FIG. 1 is an isometric view of a cardiac support device including a jacket and an attachment mechanism according to one embodiment of the present invention with the attachment mechanism in a stressed state on a heart shown in phantom lines.

FIG. 2 is an illustration of the cardiac support device of FIG. 1 with the attachment mechanism in a relaxed state.

FIG. 7 is an isometric view of a cardiac support device including a jacket and an attachment mechanism according to another embodiment of the present invention with the attachment mechanism in a stressed state.

FIG. 8 is an illustration of the cardiac support device of FIG. 7 with the attachment mechanism in a relaxed state.

FIG. 9 is an isometric view of a cardiac support device including a jacket and a fitting mechanism according to another embodiment of the present invention.

FIG. 29 is an illustration of another embodiment of a cardiac support device having a fitting mechanism in accordance with the invention.

FIG. 30 is an illustration of another embodiment of a cardiac support device having an attachment mechanism in accordance with the invention.

FIG. 33 is an illustration of another embodiment of a cardiac support device having a securing mechanism in accordance with the invention.

FIG. 34 is an illustration of another embodiment of a cardiac support device having a securing mechanism in accordance with the invention.

FIGS. 35A-35D are force-extension graphs illustrating characteristics of one embodiment of the invention.

DETAILED DESCRIPTION OF THE PREFERRED EMBODIMENTS

FIGS. 1 and 2 illustrate a cardiac support device 10 that includes a cardiac jacket 12 and a securing structure or mechanism in the form of a self-attachment structure or mechanism 14 in accordance with a first embodiment of the invention. The jacket 12 can be similar or identical to those described in any of the following U.S. patents assigned to Acorn Cardiovascular, Inc., all of which are incorporated herein by reference: U.S. Pat. Nos. 5,702,343; 6,155,972; 6,193,648; 6,482,146; 6,682,476; 6,902,524; 6,425,856; 6,908,426; 6,572,533; 6,673,009; and 6,951,534. In still other embodiments the jacket 12 can be similar or identical to those described in U.S. Pat. Nos. 6,702,732 and 6,723,041, both of which are assigned to Paracor and are incorporated herein by reference. These examples of jacket 12 are not limiting, and the securing mechanisms described herein can be incorporated into other cardiac jacket structures.

Figure 26:
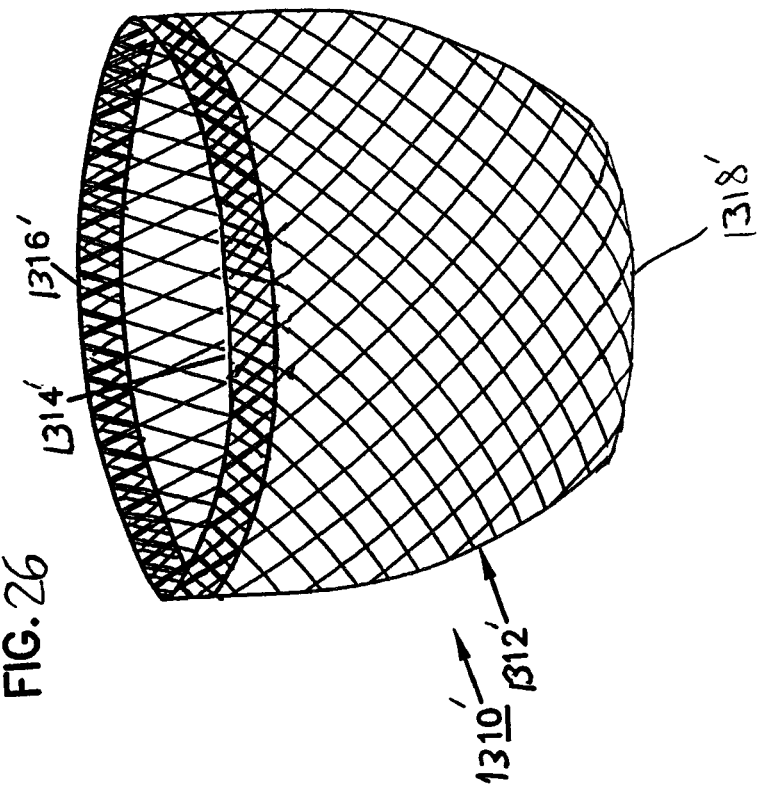
FIG. 26 is an illustration of another embodiment of a cardiac support device having an attachment mechanism in accordance with the invention.

In one preferred embodiment, the jacket 12 has a structure, compliance and elasticity, of that described in the Alfemess et al. U.S. Pat. No. 6,482,146. As shown in FIGS. 1 and 2, this embodiment of jacket 12 is a generally conical device having a base region or end 16 and an apex end 18. The base end 16 is open to permit access to the internal volume of the jacket 12. The jacket 12 can also has a base end 16 with a reinforced hem as disclosed in U.S. Pat. No. 6,155,972. The jacket material is an open-cell construction of a polyester knit material as more fully described in U.S. Pat. No. 6,482,146. In the various Figures, the apex end is shown closed. It will be appreciated the apex end 18 may be an open or closed apex (an open apex embodiment of the invention is shown in FIG. 26).

The conical jacket 12 is sized to cover the lower portion LP of a heart H (shown only in FIG. 1 in phantom lines) which would include the left and right ventricles of the heart. The jacket is typically configured so the base end 16 is sized and located to engage and surround the atrial-ventricular groove (A-V groove). In other embodiments of the invention (not shown) the jacket 12 is configured so the base end 16 is located to engage and surround portions of the heart above and/or below the A-V groove. By way of example, in other embodiments (not shown) the jacket 12 is configured to cover an upper portion UP of the heart H (which includes the left and right atria).

The attachment mechanism 14 is a circumferential and elastic structure typically located on or near a base portion such as the base end 16 of the jacket 12. In the embodiment shown in FIGS. 1 and 2, the attachment mechanism 14 is a one-piece structure that extends completely around the jacket 12. Other embodiments described below are multi-piece structures, with each piece circumferentially extending around only portions of the jacket 12. Still other embodiments (not shown) have a one undulating element that extends only partially around the circumference of the jacket 12 (e.g., about one-quarter, one-third or one-half of the jacket circumference). The elastic characteristics of the attachment mechanism 14 enable the mechanism to be expanded by an applied force from a first (e.g., neutral) state at which the mechanism has a first circumferential length or circumference (and diameter) to a second (e.g., stressed)

state at which the mechanism has a larger circumferential length or circumference (and diameter), and to return toward the first state upon the removal of the applied force. In one embodiment of the invention the elasticity of the attachment mechanism 14 is greater than the elasticity of the jacket 12. In other embodiments the attachment mechanism 14 has an elasticity that is equal to or less than the elasticity of the jacket 12. The compliance of the attachment mechanism 14 can be greater than, equal to or less than the compliance of the jacket 12.

The attachment mechanism 14 shown in FIGS. 1 and 2 is an undulating resilient element. The resilient element can, for example, be stainless steel or other metal element, or wire of these materials. Alternatively, or in addition, the undulating resilient element can include a polymer material such as elastomeric silicone. In still other embodiments the undulating resilient element is a shape memory material such as nitinol, or a wire of these materials. Other shape memory materials (e.g., polymers) can also be used for the undulating resilient elements.

In still other embodiments the undulating resilient element can be formed from or coated with a bio-resorbable material. The importance of and need for the attachment function provided by the attachment mechanism 14 can decline with time following the implantation of cardiac support device 10. For example, as a result of fibrosis, epicardial, pericardial and other tissues of the heart H adjacent to the jacket 12 will grow into and surround the material of the jacket, thereby effectively causing the jacket to be attached to the heart.

The attachment mechanism 14 can be attached directly at one or more locations to the jacket 12 by, for example, sutures, adhesive, clips or other structures. Alternatively, the attachment mechanism 14 can be retained on the jacket 12 in a free-floating form within a pocket or channel around the base end 16 of the jacket 12. For example, such a channel can be formed by a hem on the base end 16 of the jacket.

When the base end 16 of the cardiac support device 10 is stretched to increase the size of the opening from a neutral state, the attachment mechanism 14 is biased to a stressed state. In the stressed state shown in FIG. 1, the spacing $S_1$ of the undulations of the resilient element are enlarged beyond the spacing $S_2$ when in the neutral state shown in FIG. 2. With the cardiac support device 10 in the stressed state and the base end 16 opened to a size that is larger than the size of the heart H to which the device is being applied, the base end is slipped over the apex of the heart into position surrounding the valvular annulus. The force holding the attachment mechanism 14 is then released, allowing the attachment mechanism to return toward its neutral state and engage the heart H at the A-V groove. The attachment mechanism 14 thereby self-secures the jacket 12 to the heart H.

After the cardiac support device 10 is implanted on the heart H, the jacket 12 provides the therapeutic functions described in the patents identified above. The attachment mechanism 14 holds the base end 16 of the device 10 on the heart (e.g., at the A-V groove) and reduces likelihood of slippage of the device 10 following placement at the desired position on the heart. The added support of the attachment mechanism 14 at the base end 16 can be particularly advantageous in a less-invasive delivery procedure where the surgeon does not have relatively wide freedom of access to the heart.

Figure 13:
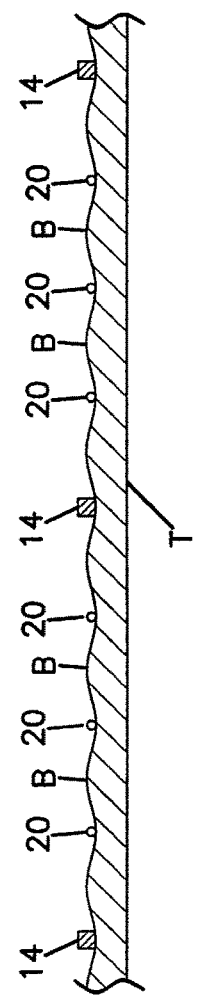
FIG. 13 is a detailed cross-sectional view of a portion of a cardiac support device shown in FIG. 12 on the epicardial surface of a heart.

Attachment mechanism 14 will typically be in a stressed state immediately following the implantation of cardiac support device 10 on a diseased heart H. Studies have shown that after a period of time following implantation, jackets 12 can cause the heart H to remodel or reduce in size. In preferred embodiments of the cardiac support device 10, the attachment mechanism 14 has a neutral state circumference that is generally equal to, but not less than, the native circumference of an equivalent-sized healthy heart. In this embodiment of the invention the forces applied to the heart H by the attachment mechanism 14 if and when the heart H is remodeled to its equivalent original size will be sufficiently low that they will not overcome the outwardly directed forces of the heart itself. In other embodiments of the invention, the attachment mechanism 14 is sized or otherwise configured so that it is in a stressed state, and overdrives the heart H to modify the heart and provide coaptation of the valve annulus geometry. The attachment mechanism 14 can add tension to the heart H at the base end 16 of the jacket 12. This tension can urge opposing tissue on the heart H to bulge into open spaces of the jacket 12. By way of example, FIG. 13 illustrates how the attachment mechanism 14 and portions 20 of jacket 12 urge against the tissue T to create bulging B in the open spaces defined between the attachment mechanism 14 and jacket portions 20. The bulges B resist movement of the jacket 12 relative to the tissue T. In still other embodiments (not shown), anchors, snares, textured friction-enhancing elements or other structures can be incorporated into the cardiac support device 10 (including attachment mechanism 14) to enhance the attachment function.

Figure 3:
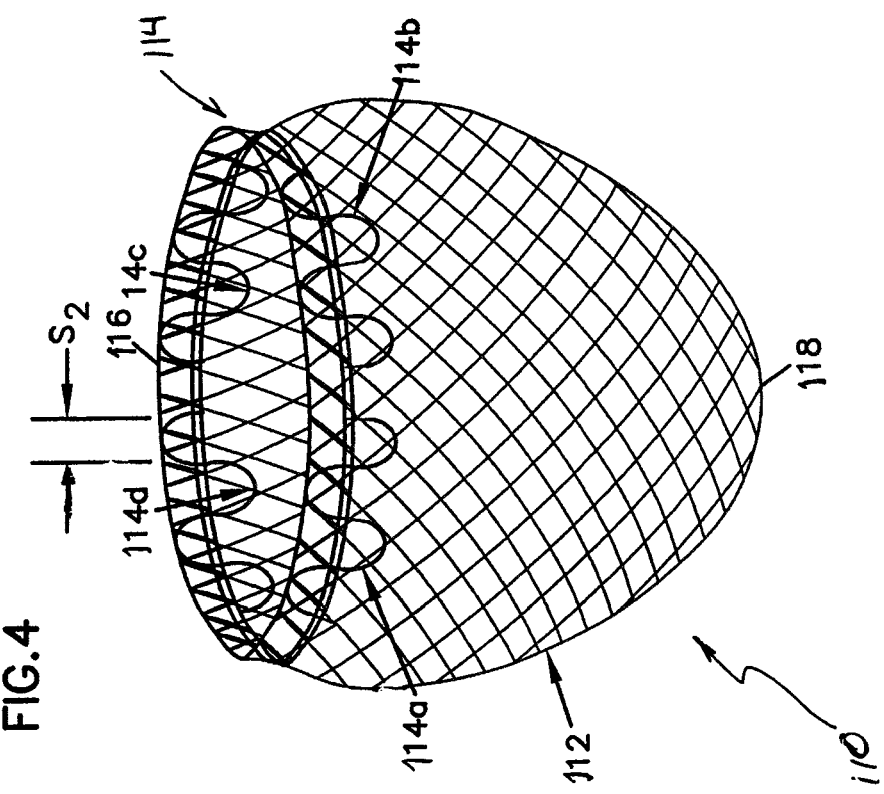
FIG. 3 is an isometric view of a cardiac support device including a jacket and an attachment mechanism according to another embodiment of the present invention with the attachment mechanism in a stressed state.
Figure 4:
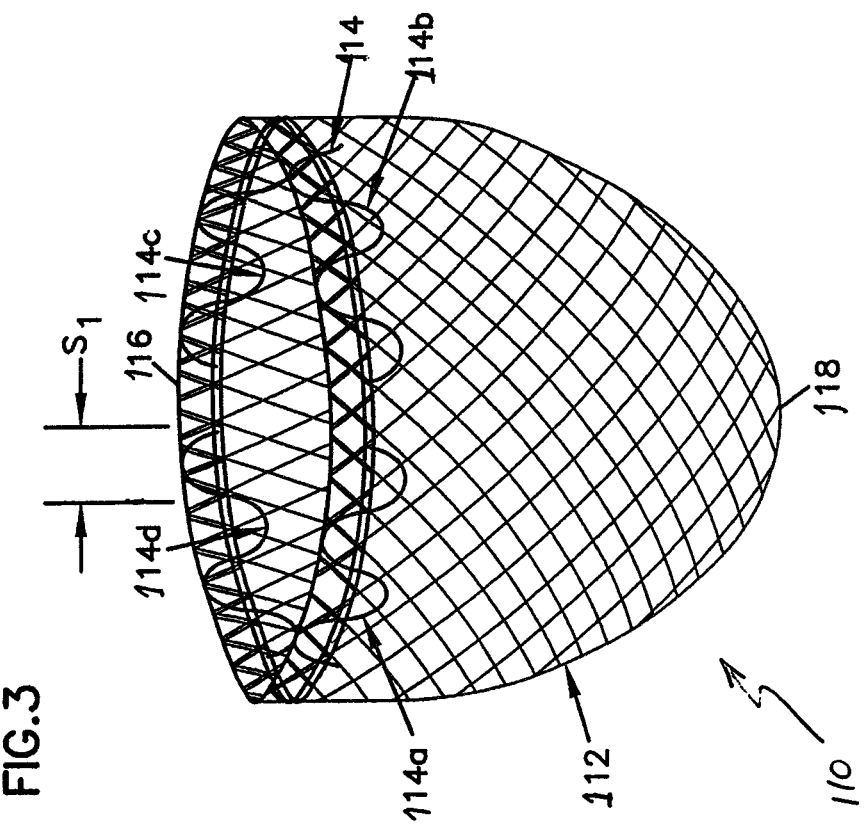
FIG. 4 is an illustration of the cardiac support device of FIG. 3 with the attachment mechanism in a relaxed state.

FIGS. 3 and 4 illustrate a cardiac support device 110 having a jacket 112 and a self-attachment structure or mechanism 114 in accordance with another embodiment of the invention. Jacket 112 can be substantially identical or similar to jacket 12 described above. Attachment mechanism 114 has a plurality (four are shown in the illustrated embodiment) of separate attachment mechanism segments 114a-114d. As shown, attachment mechanism segments 114a-114d are arranged in a circumferential pattern around the base end 116 of jacket 112. In FIG. 3, the segments 114a-114d of the attachment mechanism 114 are shown in a stressed state, stretched against their elastic bias. FIG. 4 shows the attachment mechanism 114 in a lower stress state than in FIG. 3 (e.g., in a state that the attachment mechanism can have after implantation of the cardiac support device 110 on a heart H). Other than the differences described above and illustrated in FIGS. 3 and 4, the characteristics (e.g., compliance and elasticity), function and operation of attachment mechanism 114 can be substantially identical or similar to attachment mechanism 14 described above. Similarly, the attachment mechanism 114 can be attached the jacket 112 in a manner substantially identical or similar to the above-described method by which attachment mechanism 14 is attached to jacket 12.

Figure 5:
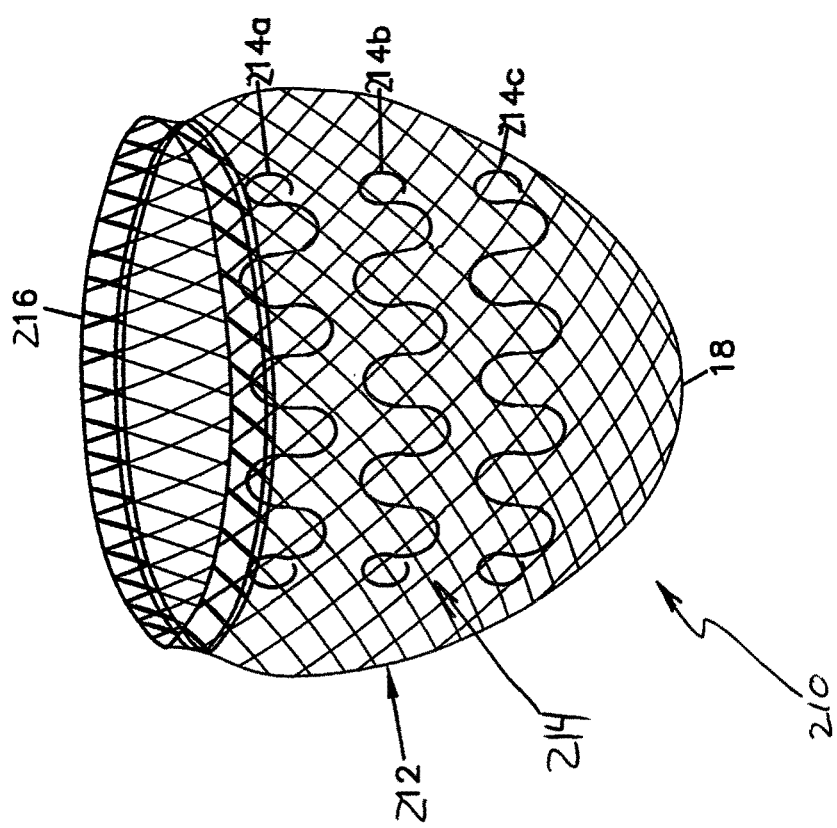
FIG. 5 is an isometric view of a cardiac support device including a jacket and a fitting mechanism according to another embodiment of the present invention with the fitting mechanism in a stressed state.
Figure 6:
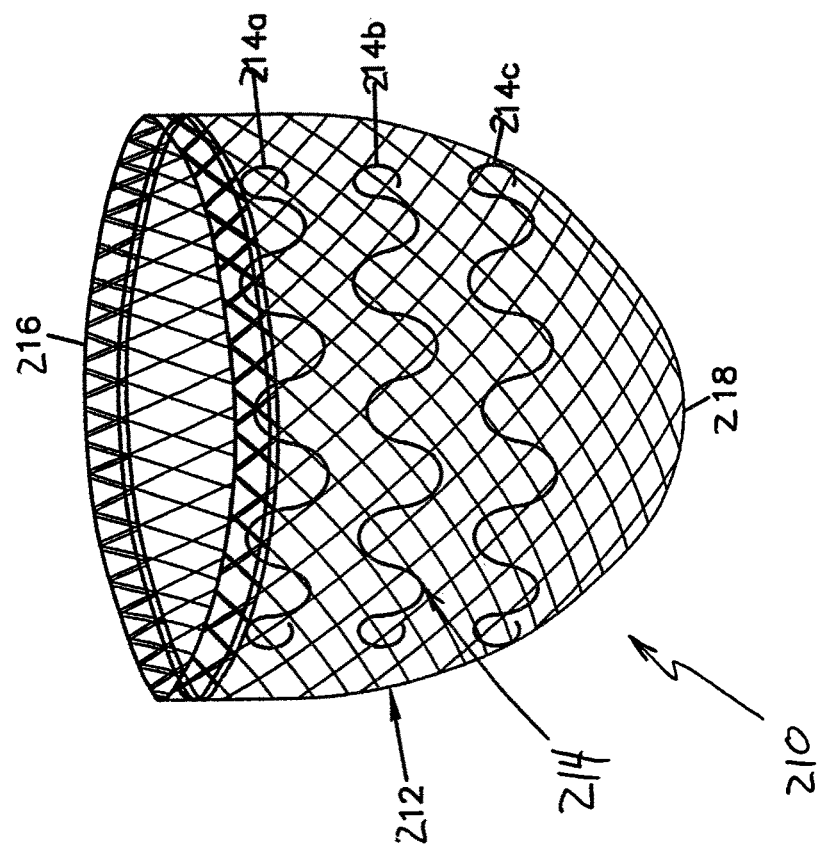
FIG. 6 is an illustration of the cardiac support device of FIG. 4 with the fitting mechanism in a relaxed state.

FIGS. 5 and 6 illustrate a cardiac support device 210 having a jacket 212 and a securing mechanism in the form of a self-fitting mechanism 214 in accordance with another embodiment of the invention. Jacket 212 can be substantially identical or similar to jacket 12 described above. Fitting mechanism 214 is an elastic structure located on the jacket 212 between the base end 216 and apex end 218. In the embodiment shown in FIGS. 5 and 6, the fitting mechanism 214 has a plurality (three are shown) of separate fitting mechanism segments 214a-214c that are spaced from one another along a generally longitudinal axis between the base end 216 and the apex end 218. Each of the fitting mechanism segments 214a-214c extends circumferentially in a generally transverse direction around a portion of the jacket 212. The elastic shape memory characteristics of the fitting mechanism 214 enable the mechanism to be expanded by an applied force from a first (e.g., neutral) state at which the mechanism has a first length to a second state at which the mechanism has a larger length, and to return toward the first state upon the removal of the applied force. In one embodiment of the invention the elasticity of the fitting mechanism 214 is greater than the elasticity of the jacket 212. In other embodiments the fitting mechanism 214 has an elasticity that is equal to or less than the elasticity of the jacket 212. The compliance of the fitting mechanism 214 can be greater than, equal to or less than the compliance of the jacket 212. In the embodiment shown in FIGS. 5 and 6 the fitting mechanism segments 214a-214c can be similar or identical in general structure to the attachment mechanism segments 114a-114d described above in connection with cardiac support device 110. However, the fitting mechanism segments 214a-214c can have differences over the attachment mechanism segments 114a-114d (e.g., different lengths, materials, elasticity and spring forces) to provide the desired fitting functionality of the fitting mechanism 214 as described below. The fitting mechanism segments 214a-214c can also be attached to the jacket 214 in ways that are substantially identical or similar to the above-described approaches by which the adjustment mechanism segments 114a-114d are attached to jacket 112. In still other embodiments (not shown) the fitting mechanism 214 can extend greater or lesser distances around, or completely around, the jacket 212.

When the cardiac support device 210 is stretched (in a generally transverse or circumferential direction) between its base end 216 and apex end 218 from its neutral state, the fitting mechanism 214 is biased to a stressed state shown in FIG. 5. The cardiac support device 210 can then be positioned on the heart H in the manner described above in connection with device 10. The force holding the fitting mechanism 214 is then released, allowing the fitting mechanism to return toward its neutral state as shown in FIG. 6.

After the cardiac support device 210 is implanted on the heart H, the fitting mechanism 214 will be in a stressed state applying a force that causes the jacket 212 be properly sized (i.e., to snugly fit) on the heart between the base end 216 and apex end 218. The fitting function provided by the fitting mechanism 214 enables the jacket 212 to provide the therapeutic functions described in the patents identified above. Although not shown in FIGS. 5 and 6, other embodiments of cardiac support device 210 also include attachment mechanisms such as those described herein.

FIGS. 7 and 8 illustrate a cardiac support device 410 having a jacket 412 and a self-attachment mechanism 414 in accordance with another embodiment of the invention. Jacket 412 can be substantially identical or similar to jacket 12 described above. Attachment mechanism 414 has a plurality (four are shown in the illustrated embodiment) of attachment mechanism rings 414a-414d. Attachment mechanism rings 414a-414d can be made from the same materials, and secured to the jacket 412 by the same approaches, as those of attachment mechanism 14 described above. The characteristics, function and operation of attachment mechanism 414 can be substantially identical or similar to those of attachment mechanism 14 described above. Briefly, when the base end 416 of the cardiac support device 410 is stretched for implantation on a heart H, the attachment mechanism rings 414a-414d will be deformed and biased to a stressed state (e.g., as shown in FIG. 7). After being implanted on a heart H, the force holding the attachment mechanism 414 is released, allowing the attachment mechanism to return toward the neutral state as shown in FIG. 8 and perform the attachment function described above.

FIG. 9 illustrates a cardiac support device 510 having a jacket 512 and a self-fitting mechanism 514 in accordance with another embodiment of the invention. Jacket 512 can be substantially identical or similar to jacket 12 described above. Cardiac support device 510 can be implanted on a heart H in a manner substantially identical or similar to that of device 210 described above. The fitting mechanism 514 is an elastic panel of material having characteristics and functions that are substantially identical or similar to those of the fitting mechanism 214 of cardiac support device 210. Fitting mechanism 514 can, for example, be a panel of material generally of the type described in the above-identified Alfemess et al. U.S. Pat. No. 6,482,146 and Girard et al. U.S. Pat. No. 6,951,534, configured to provide the desired fitting functionality of the fitting mechanism. In one embodiment, the panel of material forming fitting mechanism 514 is similar to the material forming the jacket 512, with the material of the jacket being heat set and the material of the fitting mechanism not being heat set. Heat setting processes such as those described in U.S. Pat. No. 6,951,534 provides a number of attributes to the material including an increased compliance over the material that is not heat set. The panel of material forming the fitting mechanism 514 can be sewn or otherwise attached to the adjacent portions of the jacket 512. In other embodiments (not shown) the panel of material forming the fitting mechanism 514 can overlay the material forming the jacket 512 (i.e., the panel can be an additional member on the jacket, rather than a member in place of a portion of the jacket). The shape and size of the panel of material can be selected, along with the elasticity and other characteristics of the material, to provide the desired fitting functionality. By way of example, in embodiments where the panel of material is a woven textile material such as those described in the above-identified Alfemess et al. U.S. Pat. No. 6,482,146 and Girard et al. U.S. Pat. No. 6,951,534, the different weaves or knits, and/or different thread materials, can be used to provide the desired characteristics of the material. Non-limiting examples of the shapes the panel of material include diamond, oval, ellipsoid and trapezoid. Furthermore, although not shown in FIG. 9, cardiac support device 510 can also include an attachment mechanism such as any of those described herein. The panel of fitting mechanism 514 can also extend for greater or lesser distances around the circumference of jacket 512.

Figure 11:
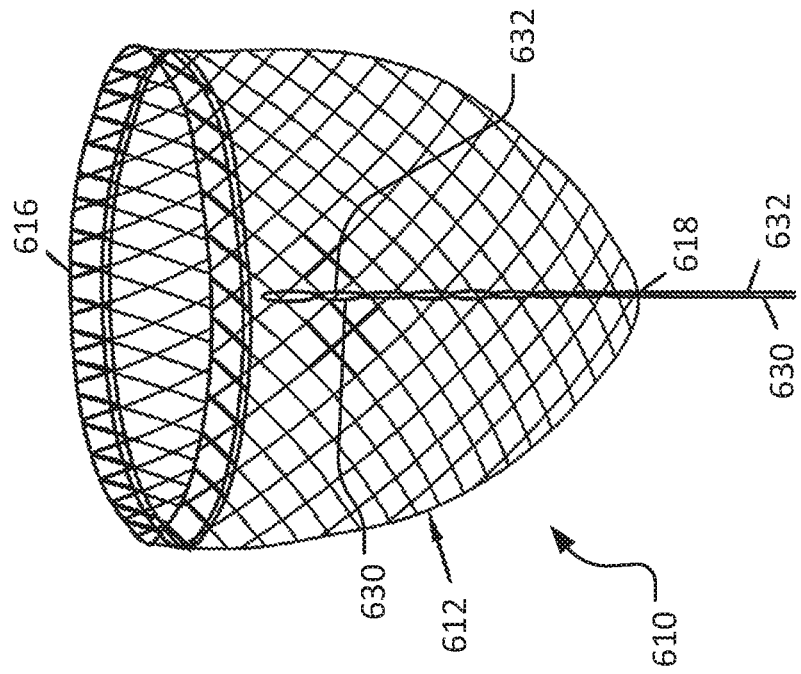
FIG. 11 is an illustration of the cardiac support device of FIG. 10 with the securing mechanism in a drawn state.
Figure 10:
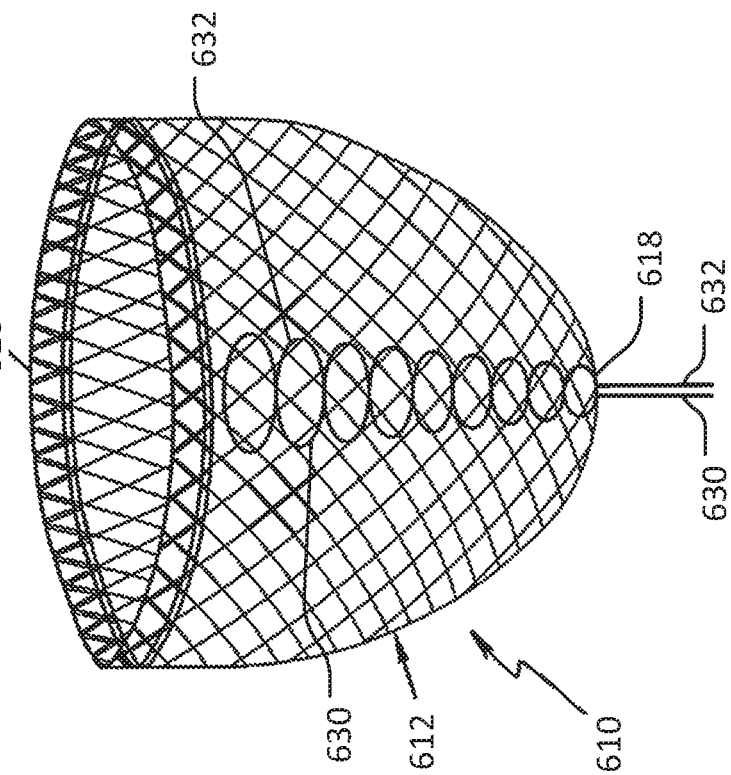
FIG. 10 is an illustration of a cardiac support device including a jacket and a securing mechanism according to another embodiment of the present invention, with the securing mechanism in a relaxed state.

FIGS. 10 and 11 illustrate a cardiac support device 610 having a jacket 612 with draw strings 630 and 632. Jacket 612 can be substantially identical or similar to jacket 12 of cardiac support device 10 described above. As shown, the draw strings 630 and 632 are incorporated into the mesh or open cell structure of the material forming the jacket 612 from a location near the base end 616 to a location near the apex end 618. As shown in FIG. 11, pulling the draw strings 630 and 632 causes the material of jacket 612 to narrow or shorten in length in the circumferential or transverse direction. Draw strings 630 and 632 can therefore be used to attach and/or fit the jacket 612 to the heart H.

Figure 12:
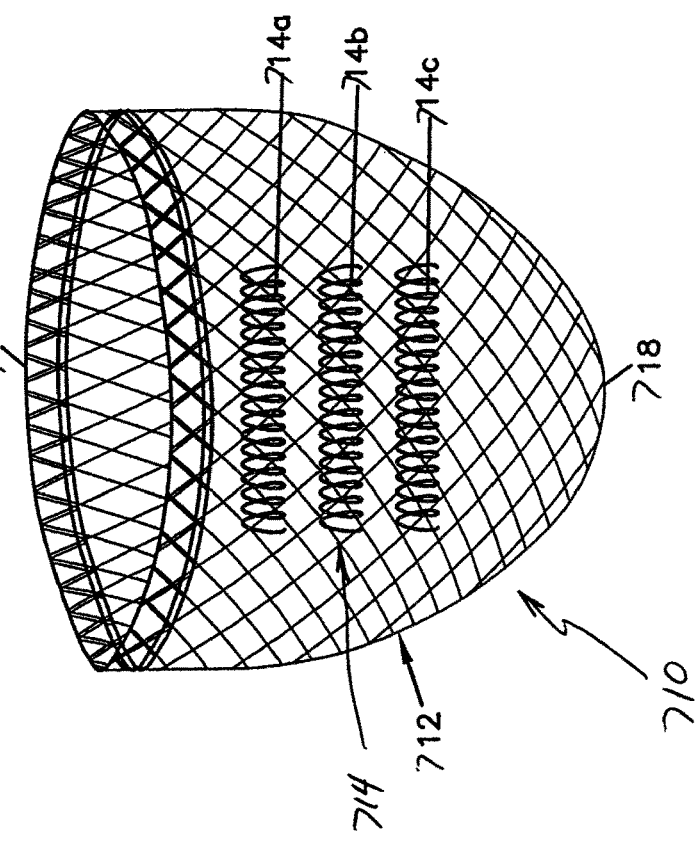
FIG. 12 is an illustration of a cardiac support device including a jacket and a fitting mechanism according to another embodiment of the present invention.

FIG. 12 illustrates a cardiac support device 710 having a jacket 712 and a self-fitting mechanism 714 in accordance with another embodiment of the invention. Jacket 712 can be substantially identical or similar to jacket 12 of cardiac support device 10 described above. Fitting mechanism 714 is an elastic structure located on the jacket 712 between the base end 716 and apex end 718. In the embodiment shown in FIG. 12, the fitting mechanism 714 has a plurality (three are shown) of separate fitting mechanism segments 714*a*-714*c* that are spaced from one another between the base end 216 and apex end 218. Each of the fitting mechanism segments 714*a*-714*c* extends circumferentially in a generally transverse direction around a portion of the jacket 712. Fitting mechanism segments 714*a*-714*c* are helical coils in the embodiment shown in FIG. 12. These helical coil fitting mechanism segments 714*a*-714*c* can be made from the same materials, and secured to the jacket 712 by the same approaches, as those of the fitting mechanism segments 214*a*-214*c* of cardiac support device 210 described above. The characteristics, functions and operation of fitting mechanism 714 can be substantially identical or similar to those of fitting mechanism 214 described above. The fitting mechanism segments 714*a*-714*c* can also extend for greater or lesser distances around the circumference of jacket 712.

Figure 15:
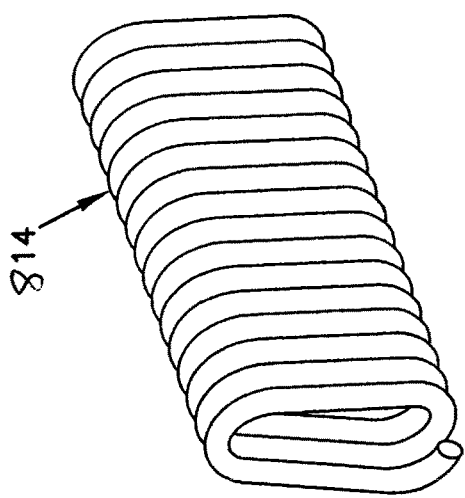
FIG. 15 is a detailed view of the attachment mechanism shown in FIG. 14.
Figure 16:
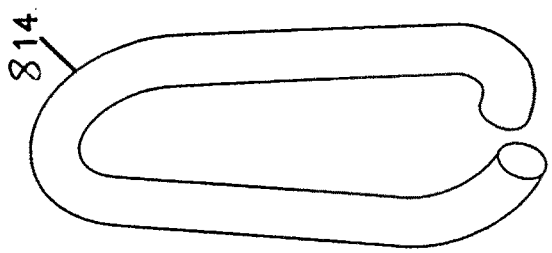
FIG. 16 is a view of a single turn of the attachment mechanism of FIG. 15.
Figure 14:
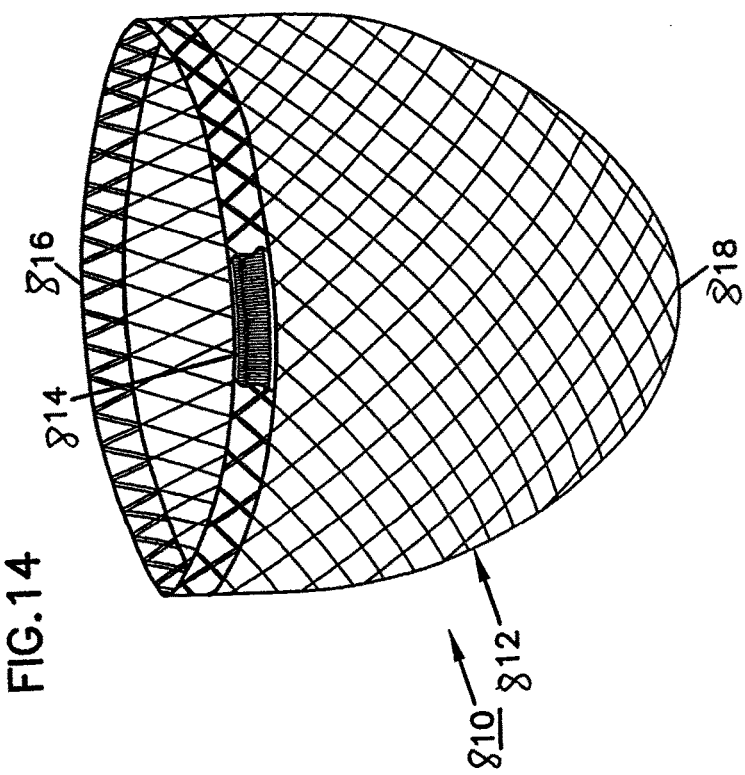
FIG. 14 is an isometric view of a cardiac support device including a jacket and an attachment mechanism according to another embodiment of the present invention, with portions of the jacket removed to show the attachment mechanism.

FIG. 14 illustrates a cardiac support device 810 having a jacket 812 and a self-attachment mechanism 814 in accordance with another embodiment of the invention. Jacket 812 can be substantially identical or similar to jacket 12 of cardiac support device 10 described above. The attachment mechanism 814 is a helical coil that extends around the base end 816 of the jacket 812. As perhaps best shown in FIGS. 15 and 16, the helical coil of attachment mechanism 814 can be flattened to provide enhanced surface area for engagement with the heart H. The helical coil of attachment mechanism 814 can be made from the same materials, and secured to the jacket 812 by the same approaches, as those of attachment mechanism 14 of cardiac support device 10 described above. The characteristics, functions and operation of attachment mechanism 814 can be substantially identical or similar to those of attachment mechanism 14 of cardiac support device 10 described above. In the embodiment shown in FIG. 14, the helical coil of attachment mechanism 814 is a single member that extends most or all of the way around the base end 816 of jacket 812. In other embodiments (not shown), the attachment mechanism 814 can have a plurality of separate helical coil segments arranged in a circumferential pattern around the base end 816 of the jacket 812 (e.g., similar to the arrangement of separate attachment mechanism segments 114*a*-114*d* of cardiac support device 110 described above), or can be a single member having two ends that extends only around a portion of the jacket 812.

Figure 18:
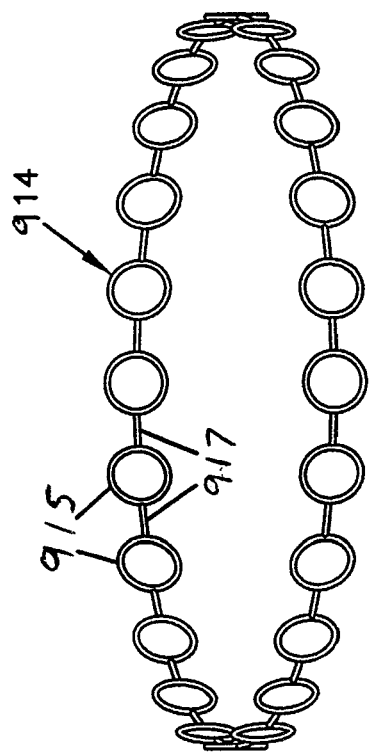
FIG. 18 is a detailed view of the attachment mechanism shown in FIG. 17.
Figure 17:
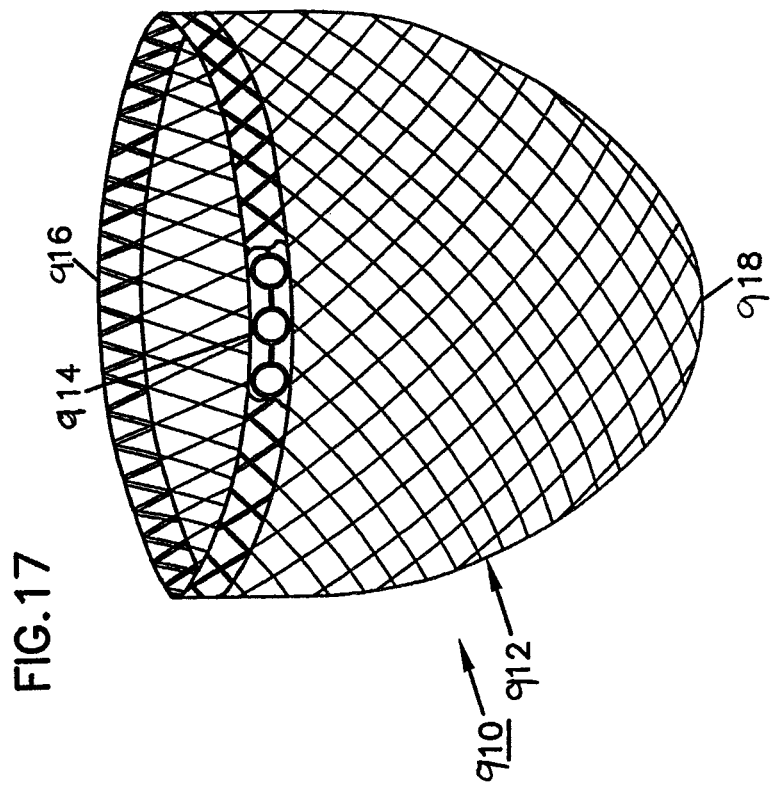
FIG. 17 is an isometric view of a cardiac support device including a jacket and an attachment mechanism according to another embodiment of the present invention.

FIG. 17 illustrates a cardiac support device 910 having a jacket 912 and a self-attachment mechanism 914 in accordance with another embodiment of the invention. Jacket 912 can be substantially identical or similar to jacket 12 of cardiac support device 10 described above. The attachment mechanism 914, which is shown in greater detail in FIG. 18, includes a plurality of rings 915 interconnected by links 917. In the illustrated embodiment, and when in the neutral state as shown in FIGS. 17 and 18, the rings 915 are circular and the links are linear. Attachment mechanism 914 can be made from the same materials, and secured to the jacket 912 by the same approaches, as those of the attachment mechanism 14 of cardiac support device 10 described above. The characteristics, functions and operation of attachment mechanism 914 can be substantially identical or similar to those of attachment mechanism 14 of cardiac support device 10 described above. Briefly, when the base end 916 of the cardiac support device 910 is stretched for implantation on a heart H, the attachment mechanism rings 915 will be deformed and biased to a stressed state (not shown). After being implanted on a heart H, the force holding the attachment mechanism 914 is released, allowing the attachment mechanism to return toward the neutral state and perform the attachment function.

Figure 20:
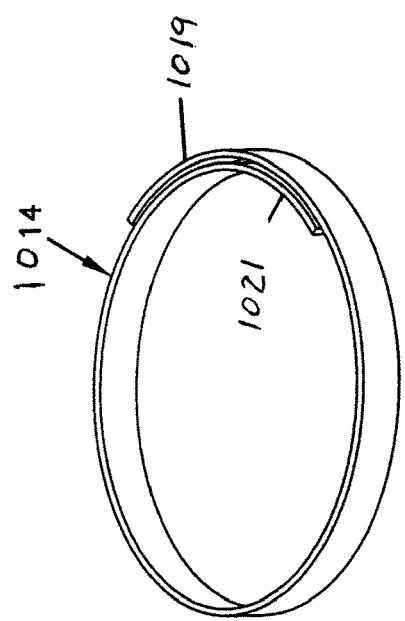
FIG. 20 is a detailed view of the attachment mechanism shown in FIG. 19.
Figure 19:
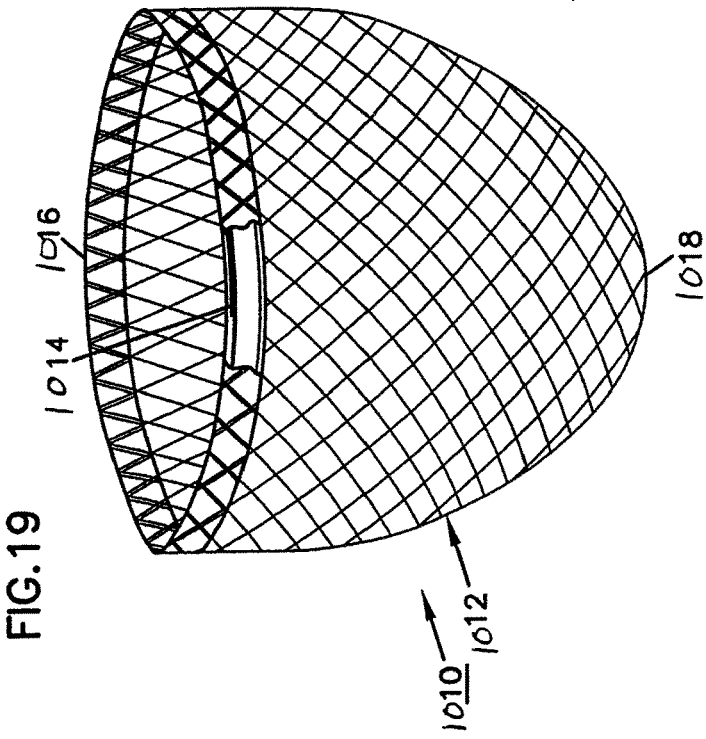
FIG. 19 is an isometric view of a cardiac support device including a jacket and an attachment mechanism according to another embodiment of the present invention, with portions of the jacket removed to show the attachment mechanism.

FIG. 19 illustrates a cardiac support device 1010 having a jacket 1012 and a self-attachment mechanism 1014 in accordance with another embodiment of the invention. Jacket 1012 can be substantially identical or similar to jacket 12 of cardiac support device 10 described above. The attachment mechanism 1014, which is shown in greater detail in FIG. 20, includes a hoop having two free ends 1019 and 1021. In the embodiment shown in FIGS. 19 and 20 the hoop is a solid member having a cross section in the shape of a generally thin and elongated polygon and a major surface that will be located adjacent to the heart H. In other embodiments (not shown, the hoop can take other forms (e.g., have apertures or a circular or other non-trapezoidal cross section). The ends 1019 and 1021 overlap in the illustrated embodiment. In other embodiments (not shown), the ends 1019 and 1021 do not overlap. Attachment mechanism 1014 can be made from the same materials, and secured to the jacket 1012 by the same approaches, as attachment mechanism 14 of cardiac support device 10 described above. The characteristics, functions and operation of attachment mechanism 1014 can be similar to those of attachment mechanism 14 of cardiac support device 10 described above. Briefly, when the base end 1016 of the cardiac support device is stretched for implantation on a heart H, the ends 1019 and 1021 move with respect to one another as the hoop is deformed and biased to a stressed state (not shown). After being implanted on a heart H, the force holding the attachment mechanism 1014 is released, allowing the attachment mechanism to return toward the neutral state and perform the attachment function.

Figure 21:
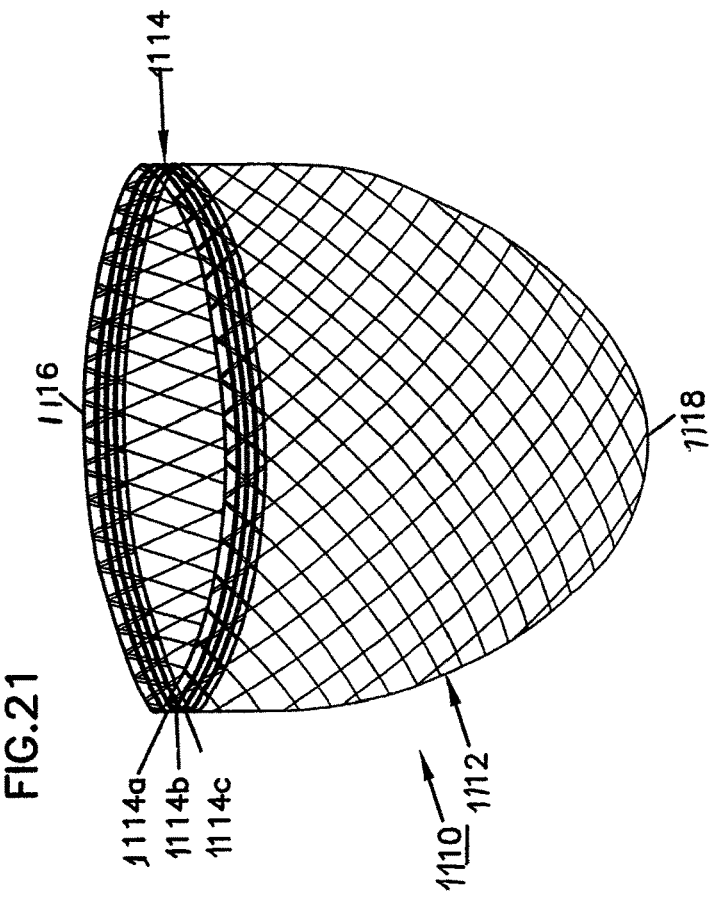
FIG. 21 is an isometric view of a cardiac support device including a jacket and an attachment mechanism according to another embodiment of the present invention.

FIG. 21 illustrates a cardiac support device 1110 having a jacket 1112 and a self-attachment mechanism 1114 in accordance with another embodiment of the invention. Jacket 1112 can be substantially identical or similar to jacket 12 of cardiac support device 10 described above. The attachment mechanism 1114 includes a plurality of filamentary or thread-like elastomeric bands 1114*a*-1114*c*. In other embodiments (not shown) the attachment mechanism 1114 has more or fewer bands 1114*a*-1114*c*. Attachment mechanism 1114 can be formed from elastomeric materials including polymers or silicone. Alternatively, the attachment mechanism 1114 can be formed from other materials in a manner that provides the elasticity and compliance characteristics. Attachment mechanism 1114 can be secured to the jacket 1112 by the same approaches as attachment mechanism 14 of cardiac support device 10 described above. The characteristics, functions and operation of attachment mechanism 1114 can be similar to those of attachment mechanism 14 of cardiac support device 10 described above.

Figure 22:
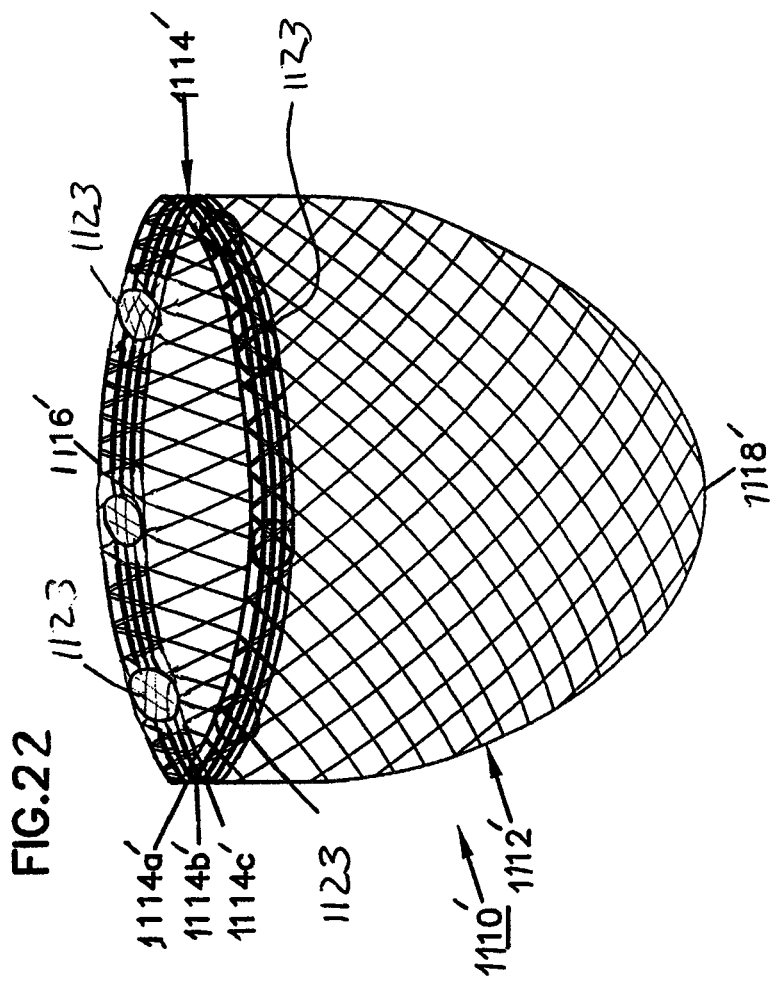
FIG. 22 is an illustration of another embodiment of a cardiac support device having an attachment mechanism in accordance with the invention.

FIG. 22 illustrates a cardiac support device 1110' having a jacket 1112' and a self-attachment mechanism 1114' in accordance with another embodiment of the invention. Attachment mechanism 1114' includes pads 1123 attached to bands 1114*a*' and 1114*c*'. Other than the addition of pads 1123, cardiac support device 1110', including attachment mechanism 1114', can be substantially identical or similar to cardiac support device 1110 described above. Pads 1123 can be formed from polymers and/or other materials such as metals, and can be attached to bands 1114*a*'-1114*c*' or jacket 1112 by sutures, adhesive, clips or other structures or approaches. Alternatively, the pads 1123 can include apertures or other structures (not shown) through which the bands 1114*a*'-1114*c*' extend. In the illustrated embodiment the pads 1123 are on the inside surface of the jacket 1112' so they will directly engage the heart H. when the cardiac support device 1110' is implanted. In other embodiments (not shown) the pads 1123 can be located so the material of the jacket 1112' will be between the pads and the heart H when the device 1110' is implanted.

Pads 1123 can facilitate the attachment of the jacket 1112' to the heart H, and can (but need not have) a structured or textured surface to enhance this functionality by increasing the friction between the pads and the heart. Examples of the types of surface structures that can be included on pads 1123 include protuberances, grit and other tissue-engaging structures such as those disclosed in the Meyer U.S. Patent Application Publication No. US 2006/0009675, which is incorporated herein by reference in its entirety.

Figure 24:
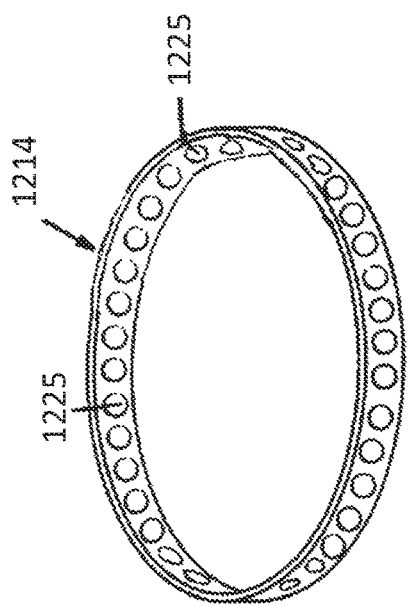
FIG. 24 is a detailed illustration of the attachment mechanism shown in FIG. 23.
Figure 23:
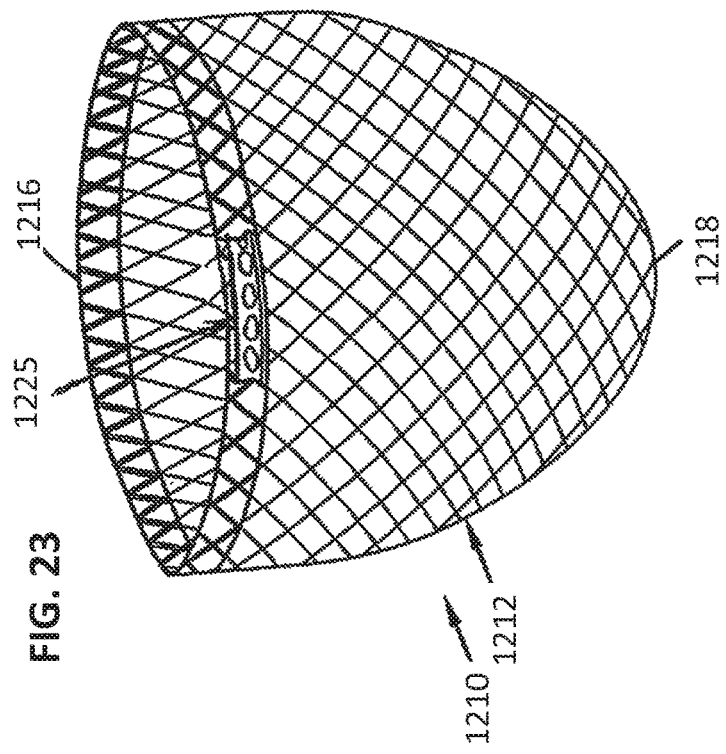
FIG. 23 is an illustration of another embodiment of a cardiac support device having an attachment mechanism in accordance with the invention.

FIG. 23 illustrates a cardiac support device 1210 having a jacket 1212 and a self-attachment mechanism 1214 in accordance with another embodiment of the invention. Jacket 1212 can be substantially identical or similar to jacket 12 of cardiac support device 10 described above. The attachment mechanism 1214, which is shown in greater detail in FIG. 24, is a band formed from elastomeric polymer or other material such as silicone, and includes a plurality of apertures 1225. The band has a cross section generally in the shape of an elongated polygon, and has a major surface that will be located adjacent to the heart H. In the illustrated embodiment, the apertures 1225 are circular when the attachment mechanism 1214 is in its neutral state. The apertures 1225 have other shapes (e.g., oval or trapezoidal) in other embodiments (not shown). Attachment mechanism 1214 can be secured to the jacket 1212 by the same approaches as attachment mechanism 14 of cardiac support device 10 described above. The characteristics, functions and operation of attachment mechanism 1214 can be substantially identical or similar to those of attachment mechanism 14 of cardiac support device 10 described above. Briefly, when the base end 1216 of the cardiac support device 1210 is stretched for implantation on a heart H, the attachment mechanism 1214, including the apertures 1225, will be deformed and biased to a stressed state (not shown). After being implanted on a heart H, the force holding the attachment mechanism 1214 is released, allowing the attachment mechanism to return toward the neutral state and perform the attachment function.

Figure 25:
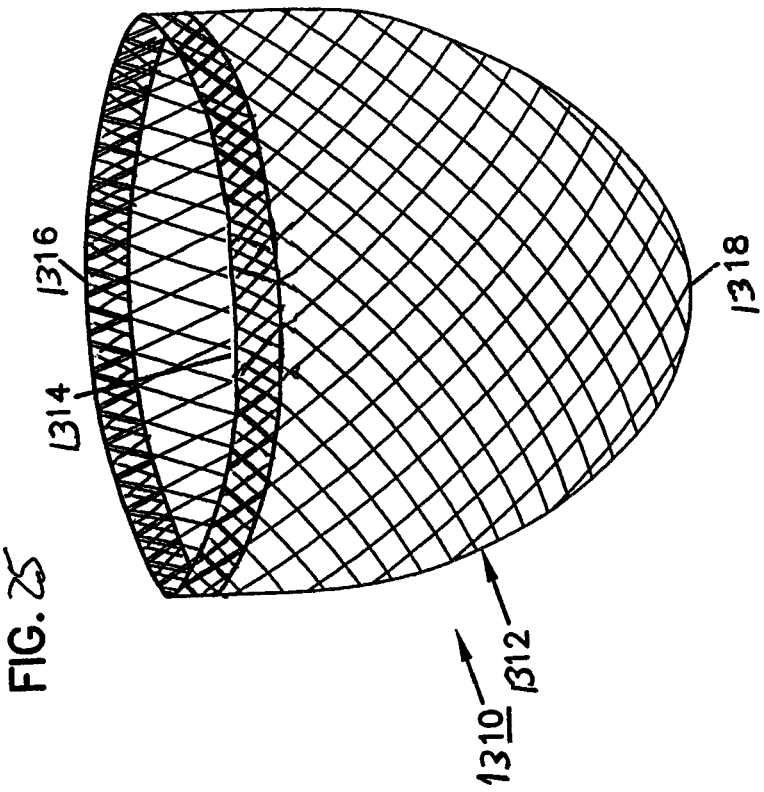
FIG. 25 is an illustration of another embodiment of a cardiac support device having an attachment mechanism in accordance with the invention.

FIG. 25 illustrates a cardiac support device 1310 having a jacket 1312 and a self-attachment mechanism 1314 in accordance with another embodiment of the invention. Jacket 1312 can be substantially identical or similar to jacket 12 of cardiac support device 10 described above. The attachment mechanism 1314 is an elastic band of open cell and preferably knit material. The material can, for example, be generally of the type described in the above-identified Alfemess et al. U.S. Pat. No. 6,482,146 and Girard et al. U.S. Pat. No. 6,951,534, configured to provide the desired attachment functionality of the attachment mechanism 1314. Like the panel of material forming fitting mechanism 514 of cardiac support device 510 described above, characteristics of the material of attachment mechanism 1314 can be controlled by heat setting or not heat setting the material. Attachment mechanism 1314 can be secured to the jacket 1312 by the same approaches as attachment mechanism 14 of cardiac support device 10 described above. Alternatively, the attachment mechanism 1314 can be attached (e.g., sewn) to the upper edge of the base end 1316 of jacket 1312, or it can be attached in an overlapping relationship with the jacket. In other embodiments the attachment mechanism 1314 can be integrally formed (e.g., interwoven) with the material of jacket 1312. The characteristics, functions and operation of attachment mechanism 1314 can be substantially identical or similar to those of attachment mechanism 14 of cardiac support device 10 described above.

FIG. 26 illustrates a cardiac support device 1310' having a jacket 1312' and a self-attachment mechanism 1314' in accordance with another embodiment of the invention. Jacket 1312' has an open apex end 1318'. With the exception of the open apex end 1318', jacket 1312' can be substantially identical or similar to jacket 1312 of cardiac support device 1310 described above. Jackets having open apex ends such as 1318' can be incorporated into any and all embodiments of the invention described herein. Also, attachment mechanism 1314' can be substantially identical or similar to attachment mechanism 1314 of cardiac support device 1310 described above.

Figure 27:
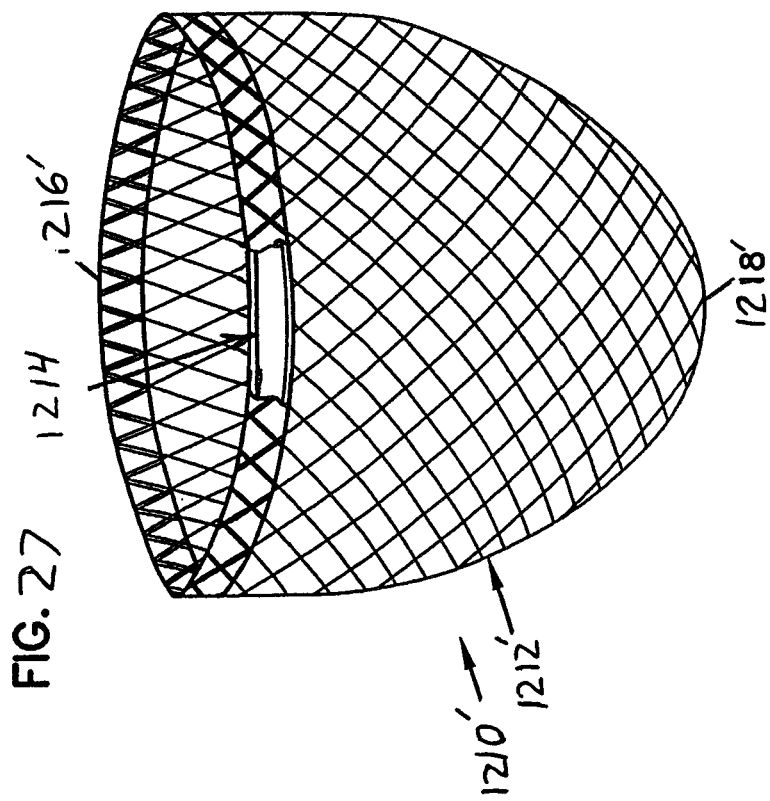
FIG. 27 is an illustration of another embodiment of a cardiac support device having an attachment mechanism in accordance with the invention.

FIG. 27 illustrates a cardiac support device 1210' having a jacket 1212' and a self-attachment mechanism 1214' in accordance with another embodiment of the invention. Jacket 1212' can be substantially identical or similar to jacket 1212 of cardiac support device 1210 described above. The attachment mechanism 1214' is a band of elastomeric polymer or other materials such as silicone, and is solid (i.e., does not contain apertures). Attachment mechanism 1214' has a cross section in the shape of a generally thin and elongated polygon and a major surface that will be located adjacent to the heart H. With the exception of its solid nature, attachment mechanism 1214' can be substantially identical or similar to attachment mechanism 1214 of cardiac support device 1210 described above. Attachment mechanism 1214' can be secured to jacket 1212' by the same approaches as attachment mechanism 1214 of cardiac support device 1210 described above.

Figure 28:
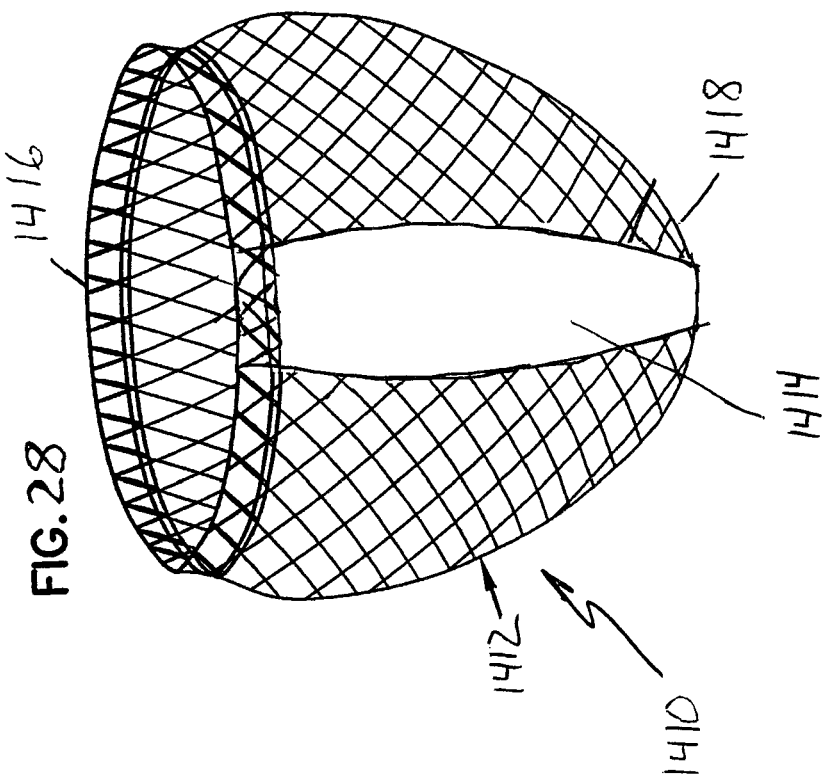
FIG. 28 is an illustration of another embodiment of a cardiac support device having a fitting mechanism in accordance with the invention.

FIG. 28 illustrates a cardiac support device 1410 having a jacket 1412 and a self-fitting mechanism 1414 in accordance with another embodiment of the invention. Jacket 1412 can be substantially identical or similar to jacket 12 of cardiac support device 10 described above. The fitting mechanism 1414 is an elastomeric panel of material having characteristics and functions that are substantially identical or similar to those of the fitting mechanism 514 of cardiac support device 510 described above. In the illustrated embodiment, fitting mechanism 1414 is a solid panel of elastomeric polymer or other material such as silicone. The panel of material forming the fitting mechanism 1414 can be sewn or otherwise attached to the adjacent portions of the jacket 1412. In other embodiments (not shown) the panel of material forming the fitting mechanism can overlay the material forming the jacket (i.e., the panel can be an additional member on the jacket, rather than a member in place of a portion of the jacket). The shape and size of the panel of material can be selected, along with the elasticity and compliance characteristics of the material, to provide the desired fitting functionality. Furthermore, although not shown in FIG. 28, cardiac support device 1410 can also include an attachment mechanism such as any of those described herein.

FIG. 29 illustrates a cardiac support device 1410' having a jacket 1412' and a self-fitting mechanism 1414' in accordance with another embodiment of the invention. Fitting mechanism 1414' includes a plurality of apertures 1427. With the exception of the apertures 1427, fitting mechanism 1414' can be substantially identical or similar to fitting mechanism 1414 of cardiac support device 1410 described above. Although shown as transversely oriented elongated members in the illustrated embodiment, the apertures 1427 can have other shapes, sizes and/or orientations. Jacket 1412' can be substantially identical or similar to jacket 1412 of the cardiac support device 1410 described above.

FIG. 30 illustrates a cardiac support device 1510 having a jacket 1512 and a self-attachment mechanism 1514 in accordance with another embodiment of the invention. Jacket 1512 can be substantially identical or similar to jacket 12 of cardiac support device 10 described above. Attachment mechanism 1514 includes one or more elastomeric filaments or threads 1529 or other elongated members interwoven into the material of the jacket 1512 at the base end 1516. The characteristics (e.g., compliance and elasticity), function and operation of attachment mechanism 1514 can be substantially identical or similar to those of attachment mechanism 14 of cardiac support device 10 described above. In the illustrated embodiment the material of jacket 1512 has an open cell form. A knit fabric of the types described above can be used for material of this type. In other embodiments (not shown) jacket 1512 is constructed of non-woven materials. In still other embodiments (not shown) the jacket 1512 is constructed of knit fabric, and the elastomeric threads 1529 or other elements are incorporated into threads of other materials from which the fabric is knit (i.e., in bundled threads).

Figure 31:
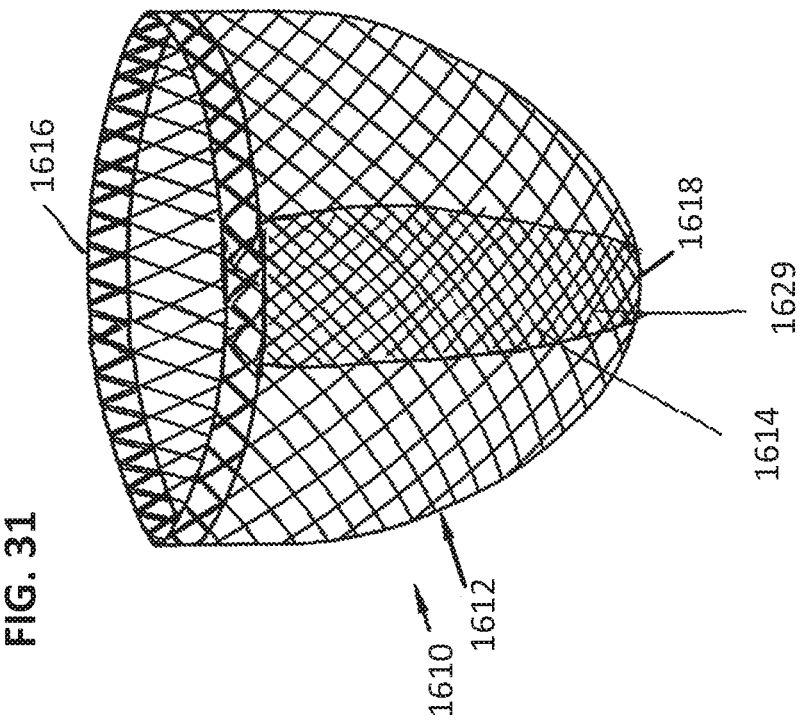
FIG. 31 is an illustration of another embodiment of a cardiac support device having a fitting mechanism in accordance with the invention.

FIG. 31 illustrates a cardiac support device 1610 having a jacket 1612 and a self-fitting mechanism 1614 in accordance with another embodiment of the invention. Jacket 1612 can be substantially identical or similar to jacket 512 of cardiac support device 510 described above. Fitting mechanism 1614 includes one or more elastomeric threads 1629 or other elongated members interwoven into the material of the jacket 1612 between the base end 1616 and apex end 1618 of the jacket. The characteristics (e.g., compliance and elasticity), function and operation of fitting mechanism 1614 can be substantially identical or similar to those of fitting mechanism 514 of cardiac support device 510 described above. In the illustrated embodiment the material of jacket 1612 is a knit fabric. In other embodiments (not shown) jacket 1612 is constructed of non-woven materials. In still other embodiments (not shown) the jacket 1612 is constructed of knit fabric, and the elastomeric threads 1629 or other elements are incorporated into threads of other materials from which the fabric is woven (i.e., in bundled threads).

Figure 32:
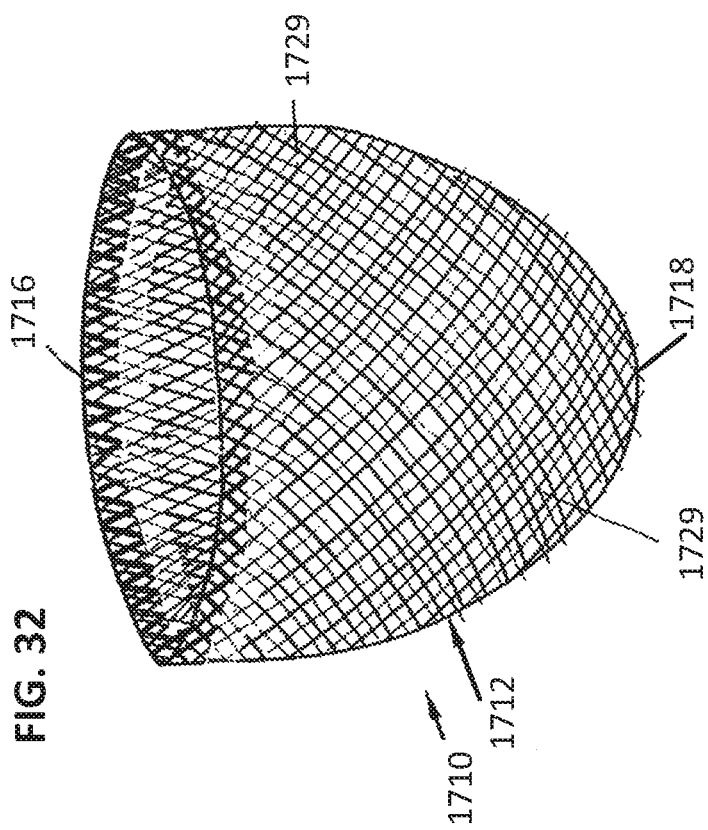
FIG. 32 is an illustration of another embodiment of a cardiac support device having a securing mechanism in accordance with the invention.

FIG. 32 illustrates a cardiac support device 1710 having a jacket 1712 and a securing mechanism 1714 in accordance with another embodiment of the invention. Jacket 1712 can be substantially identical or similar to jacket 12 of cardiac support device 10 described above. Securing mechanism 1714 includes one or more elastomeric threads 1729 or other elongated members interwoven into the material of the jacket 1712 along the base end 1716 and between the base end 1716 and apex end 1718 of the jacket. The securing mechanism 1714 effectively provides the function of both the attachment mechanisms and fitting mechanisms of the other embodiments of the invention described herein. The characteristics (e.g., compliance and elasticity), function and operation of securing mechanism 1714 can be substantially identical or similar to those of the other attachment and fitting mechanisms described herein. In the illustrated embodiment the material of jacket 1712 is a knit fabric. In other embodiments (not shown) jacket 1712 is constructed of non-woven materials. In still other embodiments (not shown) the jacket 1712 is constructed of knit fabric, and the elastomeric threads 1729 or other elements are incorporated into threads of other materials from which the fabric is woven (i.e., in bundled threads).

FIG. 33 illustrates a cardiac support device 1210" having a jacket 1212" and a self-attachment mechanism 1214" in accordance with another embodiment of the invention. Jacket 1212" can be substantially identical or similar to jacket 1212' of cardiac support device 1210' described above. The attachment mechanism 1214" is a solid band of elastomeric polymer or other materials such as silicone that has a pair of ends (i.e., is not continuous) and does not extend completely around the jacket 1212". With the exception of the fact that it is not continuous, attachment mechanism 1214" can be substantially identical or similar to attachment mechanism 1214' of cardiac support device 1210' described above. Attachment mechanism 1214" can be secured to jacket 1212" by the same approaches as attachment mechanism 1214' of cardiac support device 1210' described above. In another embodiment (not shown) the solid band of attachment mechanism 1214" extends a lesser distance around the circumference of jacket 1214". Still other embodiments (not shown) include a plurality of segments of bands such as that shown in FIG. 33 that are spaced around all or portions of the circumference of jacket 1214".

FIG. 34 illustrates a cardiac support device 1210''' having a jacket 1212''' and a self-attachment mechanism 1214''' in accordance with another embodiment of the invention. Jacket 1212''' can be substantially identical or similar to jacket 1212' of cardiac support device 1210' described above. The attachment mechanism 1214''' includes a plurality (three are shown in the illustrated embodiment) of solid bands 1214a'''-1214c''' of elastomeric polymer or other materials such as silicone. With the exception of the fact that it includes a plurality of bands 1214a'''-1214c''', attachment mechanism 1214''' can be substantially identical or similar to attachment mechanism 1214' of cardiac support device 1210' described above. The bands 1214a'''-1214c''' can have a cross section in the shape of a polygon, a circle or other shapes. In general, bands 1214a'''-1214c''' are larger in cross sectional dimension than the filamentary or thread-like elastomeric bands 1114a-1114c of attachment mechanism 1114 of cardiac support device 1110 described above. Attachment mechanism 1214''' can be secured to jacket 1212''' by the same approaches as attachment mechanism 1214' of cardiac support device 1210' described above. In another embodiment (not shown) attachment mechanism 1214''' extends a lesser distance around the circumference of jacket 1214'''. Still other embodiments (not shown) include a plurality of segments of bands such as that shown in FIG. 34 that are spaced around all or portions of the circumference of jacket 1214'''.

An example of the operation of one embodiment of the attachment mechanism 14 and jacket 12 of a cardiac support device 10 can be described with reference to FIGS. 35A-35D. FIG. 35A is a graph of the force/extension curve of one embodiment of the attachment mechanism 14. FIG. 35B is a graph of the force/extension curve of the base end 16 of one embodiment of the jacket 12. In this example of cardiac support device 10, the slope of the force/extension curve of the jacket base end 16 is steeper than that of the attachment mechanism 14. FIG. 35C is an illustration of the force/extension curves shown in FIGS. 35A and 35C superimposed on one another in a manner that represents the operational relationship between these curves in the cardiac support device 10. As shown, the zero force locations of the force/extension curves are at different extension locations (i.e., the curves have differential starting points). This characteristic represents the fact that for this embodiment of cardiac support device 10, the attachment mechanism 14 will be in a stressed (e.g., expanded) state when the jacket 12 is in its neutral (e.g., un-stressed) state. FIG. 35D is a graph of the composite force/extension curve of the cardiac support device 10. The marker in FIG. 35D illustrates where the jacket 12 effectively begins contributing to the curve. As is evident from FIGS. 35C and 35D, while the jacket 12 is in its neutral (and possibly collapsed) state, the force applied by the cardiac support device 10 is all provided by the attachment mechanism 14. For an initial range of expansion of the jacket 12 beyond its neutral point, the force applied by the jacket is less than that applied by the attachment mechanism 14, so the overall force applied by the cardiac support device 10 is dominated by that provided by the attachment mechanism. With continued expansion of the jacket 12, the force applied by the jacket will reach a point where it equals the force applied by the attachment mechanism 14. When the jacket 12 is expanded beyond the point where the force applied by the jacket 12 equals the force applied by the attachment mechanism 14, the overall force applied by the cardiac support device 10 will be dominated by that provided by the jacket. The relative forces applied by the attachment mechanism 14 and jacket 12 in other embodiments of the invention can be different than those shown in FIGS. 35A-35D. The relative forces applied by the jacket and fitting structures of other embodiments of the invention can also be similar to those illustrated in FIGS. 35A-35D.

Although the present invention has been described with reference to preferred embodiments, those skilled in the art will recognize that changes can be made in form and detail without departing from the spirit and scope of the invention. In particular, any self-attachment mechanisms of the invention can be combined on the same jacket with any of the self-fitting mechanisms of the invention to produce additional embodiments of cardiac support devices having securing mechanism in accordance with the invention. Cardiac support devices in accordance with the invention can be implanted on the heart using any desired approaches including minimally-invasive and open chest procedures.

What is claimed is:

1. A cardiac support device including:
    a compliant jacket comprising a knit material and having base and apex regions, the jacket being circumferentially closed between the base and apex regions, the base region defining an open end, the jacket configured for surrounding at least a lower portion of a heart and constraining cardiac expansion; and
    means for self-fitting the jacket to the heart attached directly at one or more locations to the jacket and at the open end of the base region of the jacket, wherein the means: (i) is configured to be positioned in an atrial-ventricular groove of the heart, (ii) is configured for holding the open end in the atrial-ventricular groove of the heart to self-secure the jacket to the heart, and (iii) extends continuously around the base region to provide self-adjusting fitting of the open end in the atrial-ventricular groove of the heart around an entire circumference of the base region.

2. The cardiac support device of claim 1, wherein the cardiac support device is configured to be implanted on the heart using a minimally invasive approach and to become attached to the heart by tissue fibrosis.

3. The cardiac support device of claim 1, wherein the jacket is elastic.

4. The cardiac support device of claim 1, wherein the means for holding the open end in the atrial-ventricular groove comprises an elastic attachment band.

5. The cardiac support device of claim 4, wherein the elastic attachment band comprises a polymer band.

6. The cardiac support device of claim 4, wherein the elastic attachment band extends completely around the jacket.

7. The cardiac support device of claim 4, wherein the elastic attachment band is attached to the jacket within a channel defined at the base region.

8. The cardiac support device of claim 7, wherein the channel defines the open end.

9. The cardiac support device of claim 7, wherein the channel comprises a hem of the knit material.

* * * * *